US011782373B2

(12) United States Patent
 Kato

(10) Patent No.: US 11,782,373 B2
(45) Date of Patent: Oct. 10, 2023

(54) IMAGE FORMING APPARATUS WITH FUNCTION OF PREVENTING SECONDARY INFECTION

(71) Applicant: TOSHIBA TEC KABUSHIKI KAISHA, Tokyo (JP)

(72) Inventor: Tetsuo Kato, Yokohama Kanagawa (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 92 days.

(21) Appl. No.: 17/570,408

(22) Filed: Jan. 7, 2022

(65) Prior Publication Data

US 2023/0221668 A1  Jul. 13, 2023

(51) Int. Cl.
*G03G 15/00* (2006.01)
*G06K 15/00* (2006.01)
*H04N 1/00* (2006.01)
*A61B 5/01* (2006.01)

(52) U.S. Cl.
CPC ........... *G03G 15/5016* (2013.01); *A61B 5/01* (2013.01); *G06K 15/002* (2013.01); *G06K 15/407* (2013.01); *G06K 15/4085* (2013.01); *H04N 1/00411* (2013.01); *H04N 1/00514* (2013.01); *A61B 2503/20* (2013.01)

(58) Field of Classification Search
CPC .. G03G 15/5016; A61B 5/01; A61B 2503/20; G06K 15/002; G06K 15/407; G06K 15/4085; H04N 1/00411; H04N 1/00514
See application file for complete search history.

(56) References Cited

U.S. PATENT DOCUMENTS

2014/0368855 A1* 12/2014 Yamano ................ G06F 1/3284
                                                    358/1.13
2020/0053234 A1*  2/2020 Takahashi .......... H04N 1/00323

FOREIGN PATENT DOCUMENTS

| JP | 2006-091687 | 4/2006 |
| JP | 2016-020933 | 2/2016 |
| JP | 2017-204672 | 11/2017 |
| JP | 2018-084974 | 5/2018 |
| JP | 2018-084975 | 5/2018 |

* cited by examiner

*Primary Examiner* — Hoang X Ngo
(74) *Attorney, Agent, or Firm* — AMIN, TUROCY & WATSON, LLP

(57) ABSTRACT

An image forming apparatus for forming an image on paper includes a body surface temperature measuring sensor, a user interface, a communication interface, and a controller. The body surface temperature measuring sensor measures the body surface temperature of the operator in a non-contact manner. The user interface presents a message to the operator. The communication interface transmits a message to the administrator who manages the image forming apparatus. When access to the surface or the inside of the image forming apparatus is required and the body surface temperature of the operator is equal to or higher than a threshold temperature, the controller transmits a message requesting to touch the surface or the inside of the image forming apparatus to the administrator by the communication interface and presents a message requesting not to touch the image forming apparatus to the operator by the user interface.

20 Claims, 14 Drawing Sheets

IMAGE FORMING APPARATUS WITH FUNCTION OF PREVENTING SECONDARY INFECTION

FIELD

Embodiments described herein relate generally to an image forming apparatus with the function of preventing a secondary infection.

BACKGROUND

The image forming apparatus forms an image on paper. In the related art, an input operation using a touch panel is required to operate the image forming apparatus. If a person with an infectious disease who has been infected with an infectious disease such as influenza or norovirus operates the touch panel, the virus adheres to the operated part. Therefore, if a person without an infectious disease who is not infected with an infectious disease subsequently operates the touch panel, the virus adheres to the finger of the person without an infectious disease, so that the person without an infectious disease is infected and the infectious disease is sometimes widespread.

For this reason, a technique has been proposed that enables a person without an infectious disease to operate without touching the touch panel area touched by a person with an infectious disease. For example, a technique has been proposed to prevent infection by identifying an area touched by a person with an infectious disease, setting it as a contaminated area, and moving the display of operation buttons to a non-contaminated area. In addition, a technique also has been proposed in which whether the operator is a person with an infectious disease or a person without an infectious disease is determined by the movement of the operator (sneezing, coughing, wearing a mask) by a surveillance camera and a person without an infectious disease is prevented from touching the operation button part contaminated by a person with an infectious disease.

However, the technique proposed in the related art is a countermeasure against virus adhesion to the operation input unit and is not able to deal with virus adhesion to the surface or the inside of the image forming apparatus by touching the surface or the inside of the image forming apparatus in the replenishment and replacement work of consumables.

DETAILED DESCRIPTION

In general, according to one embodiment, the image forming apparatus for forming an image on paper includes a body surface temperature measuring sensor, a user interface, a communication interface, and a controller. The body surface temperature measuring sensor measures the body surface temperature of the operator in a non-contact manner. The user interface presents a message to the operator. The communication interface transmits a message to the administrator who manages the image forming apparatus. When access to the surface or the inside of the image forming apparatus is required and the body surface temperature of the operator is equal to or higher than a threshold temperature, the controller transmits a message requesting to touch the surface or the inside of the image forming apparatus to the administrator by the communication interface and presents a message requesting not to touch the image forming apparatus to the operator by the user interface.

Hereinafter, embodiments of the present invention will be described in detail with reference to the drawings.

Figure 1:
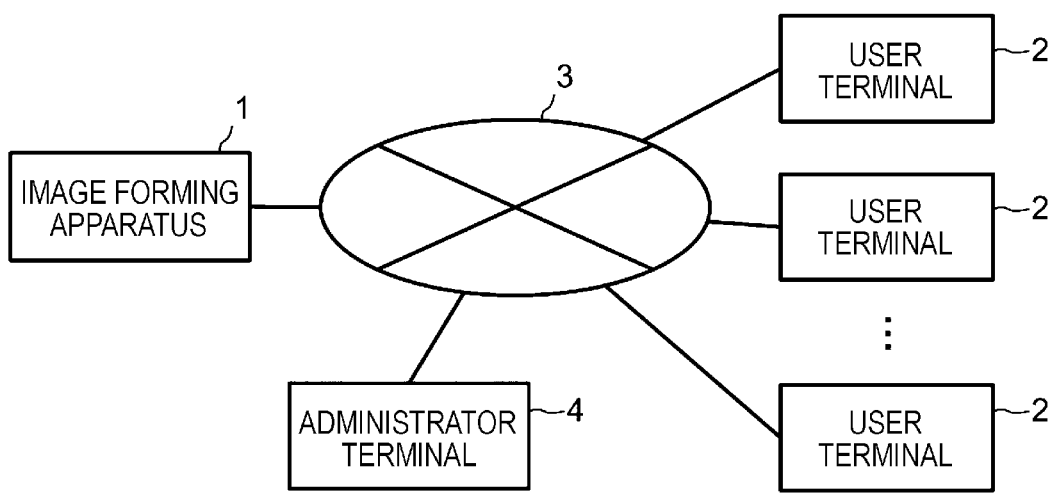
FIG. 1 is a block diagram showing an example of a configuration of an image forming system including an image forming apparatus according to an embodiment.

FIG. 1 is a block diagram showing an example of a configuration of an image forming system including an image forming apparatus according to an embodiment. The image forming apparatus 1 is connected to one or more user terminals 2 via a network 3. Further, the image forming apparatus 1 is also connected to the administrator terminal 4 via the network 3.

In the present embodiment, a multifunction peripheral (MFP) will be described as an example of the image forming apparatus 1. The MFP is an apparatus having multiple functions such as a function of forming a desired image on a print medium which is a sheet-like paper such as paper or a resin sheet, that is, a function of printing, a function of reading an image formed on the print medium based on image information composed of electronic data, and the like. The MFP may further have the function of a facsimile machine.

The user terminal 2 is a personal computer or the like that generates image data to be printed and transmits the generated image data to the image forming apparatus 1.

The network 3 is, for example, a wired Local Area Network (LAN) or a wireless LAN configured in-house.

The administrator terminal 4 is a terminal of an administrator who manages consumables in the image forming apparatus 1 and replenishes and replaces consumables to the image forming apparatus 1. The administrator terminal 4 is a personal computer or the like. One of the user terminals 2 can also serve as the administrator terminal 4.

Figure 2:
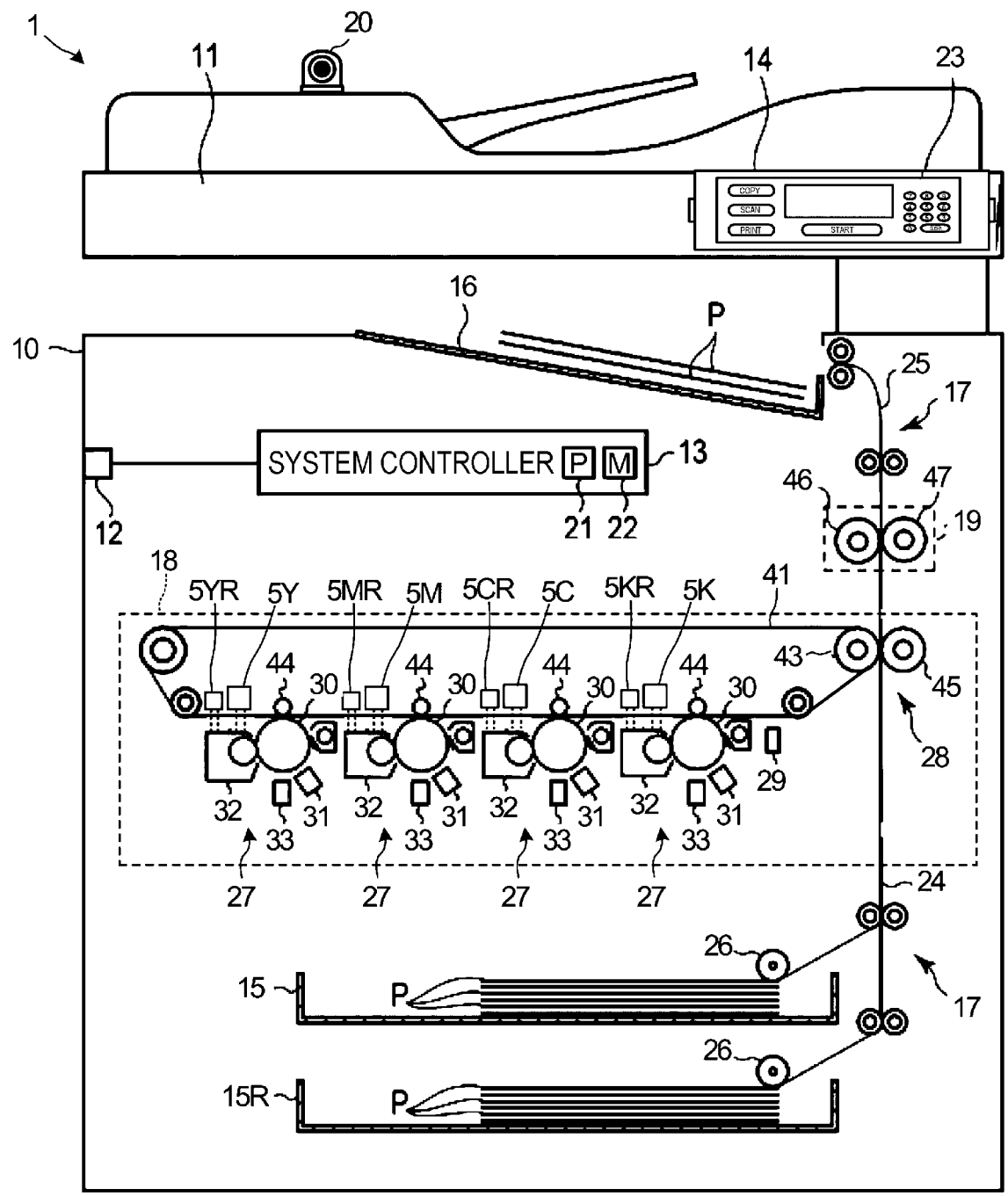
FIG. 2 is a schematic diagram showing an example of the internal configuration of the image forming apparatus.

FIG. 2 is a schematic diagram showing an example of the internal configuration of the image forming apparatus. The image forming apparatus 1 has, for example, a configuration in which a low-temperature fixing toner using a crystalline polyester resin is replenished from a toner cartridge to form an image on a print medium. The toner is, for example, a toner selected from cyan (C), magenta (M), yellow (Y), black (K), and the like. The image forming apparatus 1 can also select one toner and form a monochromatic image with that toner on a print medium. The toner may be a decolorizable toner.

The image forming apparatus 1 can mount a toner cartridge 5C containing cyan toner which is a chromatic toner, a toner cartridge 5M containing magenta toner, a toner cartridge 5Y containing yellow toner, and a toner cartridge 5K containing black toner. In other words, the toner cartridges 5C, 5M, 5Y, and 5K can be taken out from the image forming apparatus 1 and replaced. In the following description, if it is not necessary to distinguish between the toner cartridges 5C, 5M, 5Y, and 5K, the toner cartridges 5C, 5M, 5Y, and 5K are referred to as the toner cartridge 5.

Further, the image forming apparatus 1 can mount spare toner cartridges 5CR, 5MR, 5YR, and 5KR as spares for these toner cartridges 5. In other words, the spare toner cartridges 5CR, 5MR, 5YR, and 5KR can be taken out from the image forming apparatus 1 and replaced. In the following description, if it is not necessary to distinguish between the spare toner cartridges 5CR, 5MR, 5YR, and 5KR, the spare toner cartridges 5CR, 5MR, 5YR, and 5KR are referred to as the spare toner cartridge 5R. The spare toner cartridge 5R is used if the operator is a person with a fever and the remaining amount of toner contained in the toner cartridge 5 ran out. If the operator is a person without a fever, the toner contained in the spare toner cartridge 5R is not used.

As shown in FIG. 2, the image forming apparatus 1 includes a housing 10, an image reading unit 11, a communication interface 12, a system controller 13, an operation unit 14, a paper cassette 15, a spare paper cassette 15R, a paper discharge tray 16, a conveyance unit 17, an image forming unit 18, a fixing device 19, and an infrared thermography camera 20.

The housing 10 is the main body of the image forming apparatus 1. The housing 10 houses the image reading unit 11, the communication interface 12, the system controller 13, the operation unit 14, the paper cassette 15, the spare paper cassette 15R, the paper discharge tray 16, the conveyance unit 17, the image forming unit 18, the fixing device 19, and the infrared thermography camera 20.

The image reading unit 11 acquires characters, illustrations, photographs, or the like on the object to be read based on brightness and darkness, and generates image data corresponding to the brightness and darkness. The image reading unit 11 includes at least a document table (document glass), a lighting device, and an image sensor. The lighting device irradiates the document supported by the document table, that is, the object to be read, with illumination light. The image sensor receives the reflected light (image information) reflected by the document and performs photoelectric conversion to generate an image signal. The image sensor is, for example, a CCD sensor or a Complementary metal-oxide Semiconductor (CMOS) sensor.

The communication interface 12 is an interface for communicating with other devices. The communication interface 12 is used, for example, for communication with the user terminal 2 and the administrator terminal 4, which are higher-level devices (external devices). The communication interface 12 is configured as, for example, a LAN connector for connecting to a wired LAN. The communication interface 12 may perform wireless communication with other devices directly or via a wireless LAN according to a standard such as Bluetooth (registered trademark) or Wi-fi (registered trademark).

The system controller 13 controls the image forming apparatus 1. The system controller 13 includes, for example, a processor 21 and a memory 22. Further, the system controller 13 is connected to the image reading unit 11, the conveyance unit 17, the image forming unit 18, the fixing device 19, the infrared thermography camera 20, and the like via a bus or the like.

The processor 21 is an arithmetic element that executes arithmetic processing. The processor 21 is, for example, a microprocessor (MPU). The processor 21 performs various processes based on data such as a program stored in the memory 22. The processor 21 functions as a control unit capable of executing various operations by executing a program stored in the memory 22.

The processor 21 controls the conveyance unit 17, the image forming unit 18, the fixing device 19, and the infrared thermography camera 20 by executing the program stored in the memory 22. The processor 21 executes a program stored in the memory 22 to generate a print job for forming an image on a print medium P. For example, the processor 21 generates a print job based on an image acquired from the user terminal 2 via the communication interface 12. The processor 21 may generate a print job based on the image read by the image reading unit 11, for example. The processor 21 stores the generated print job in the memory 22.

The print job includes image data indicating an image formed on the print medium P. The image data may be data for forming an image on one print medium P or may be data for forming an image on a plurality of print media P. In addition, the print job contains information indicating whether it is a color print or a monochrome print.

The operation unit 14 includes a liquid crystal touch panel 23. The liquid crystal touch panel 23 includes a liquid crystal display that displays a screen in response to a video signal input from a display control unit such as the system controller 13 or a graphic controller (not shown). For example, the liquid crystal display of the liquid crystal touch panel 23 displays screens for various settings of the image forming apparatus 1. Further, the liquid crystal touch panel 23 includes a touch sensor arranged on the liquid crystal display. The touch sensor supplies an operation signal corresponding to the touch position of the operator to the system controller 13.

The paper cassette 15 and the spare paper cassette 15R are cassettes that accommodate the print medium P, respectively. The paper cassette 15 and the spare paper cassette 15R are configured so that the print medium P can be supplied from the outside of the housing 10. For example, the paper cassette 15 and the spare paper cassette 15R are configured to be retractable from the housing 10. The spare paper cassette 15R is used if the operator is a person with a fever and the print medium P of the paper cassette 15 ran out. If the operator is a person without a fever, the print medium P contained in the spare paper cassette 15R is not used. Although only one paper cassette 15 is shown in FIG. 2, the image forming apparatus 1 may include a plurality of paper cassettes 15.

The paper discharge tray 16 is a tray that supports the print medium P discharged from the image forming apparatus 1.

The conveyance unit 17 is a mechanism for conveying the print medium P in the image forming apparatus 1. As shown in FIG. 2, the conveyance unit 17 includes a plurality of conveyance paths. For example, the conveyance unit 17 includes a paper feed conveyance path 24 and a paper discharge conveyance path 25.

The paper feed conveyance path 24 and the paper discharge conveyance path 25 are each composed of a plurality of motors, a plurality of rollers, and a plurality of guides (not shown). The plurality of motors rotate the shaft under the control of the system controller 13 to rotate the rollers linked to the rotation of the shaft. The plurality of rollers move the print medium P by rotating. The plurality of guides control the conveyance direction of the print medium P.

The paper feed conveyance path 24 picks up the print medium P from the paper cassette 15 or the spare paper cassette 15R and supplies the picked-up print medium P to the image forming unit 18. The paper feed conveyance path 24 includes a pickup roller 26 corresponding to each paper cassette. Each pickup roller 26 introduces the print medium P of the paper cassette 15 or the spare paper cassette 15R into the paper feed conveyance path 24.

The paper discharge conveyance path 25 is a conveyance path for discharging the print medium P on which the image was formed from the housing 10. The print medium P discharged by the paper discharge conveyance path 25 is supported by the paper discharge tray 16.

Next, the image forming unit 18 will be described. The image forming unit 18 is configured to form an image on the print medium P based on the control of the system controller 13. Specifically, the image forming unit 18 forms an image on the print medium P based on the print job generated by the processor 21. The image forming unit 18 includes a plurality of process units 27, a transfer mechanism 28, and a temperature and humidity sensor 29.

First, the configuration related to the image formation of the image forming unit 18 will be described. The plurality of process units 27 correspond to cyan toner, magenta toner, yellow toner, and black toner, respectively. The toner cartridges 5 (toner cartridges 5C, 5M, 5Y, and 5K) and the spare toner cartridges 5R (spare toner cartridges 5CR, 5MR, 5YR, and 5KR) having toners of different colors are connected to each process unit 27. Since the plurality of process units 27 have the same configuration except for the developer to be filled, one process unit 27 will be described.

Figure 3:
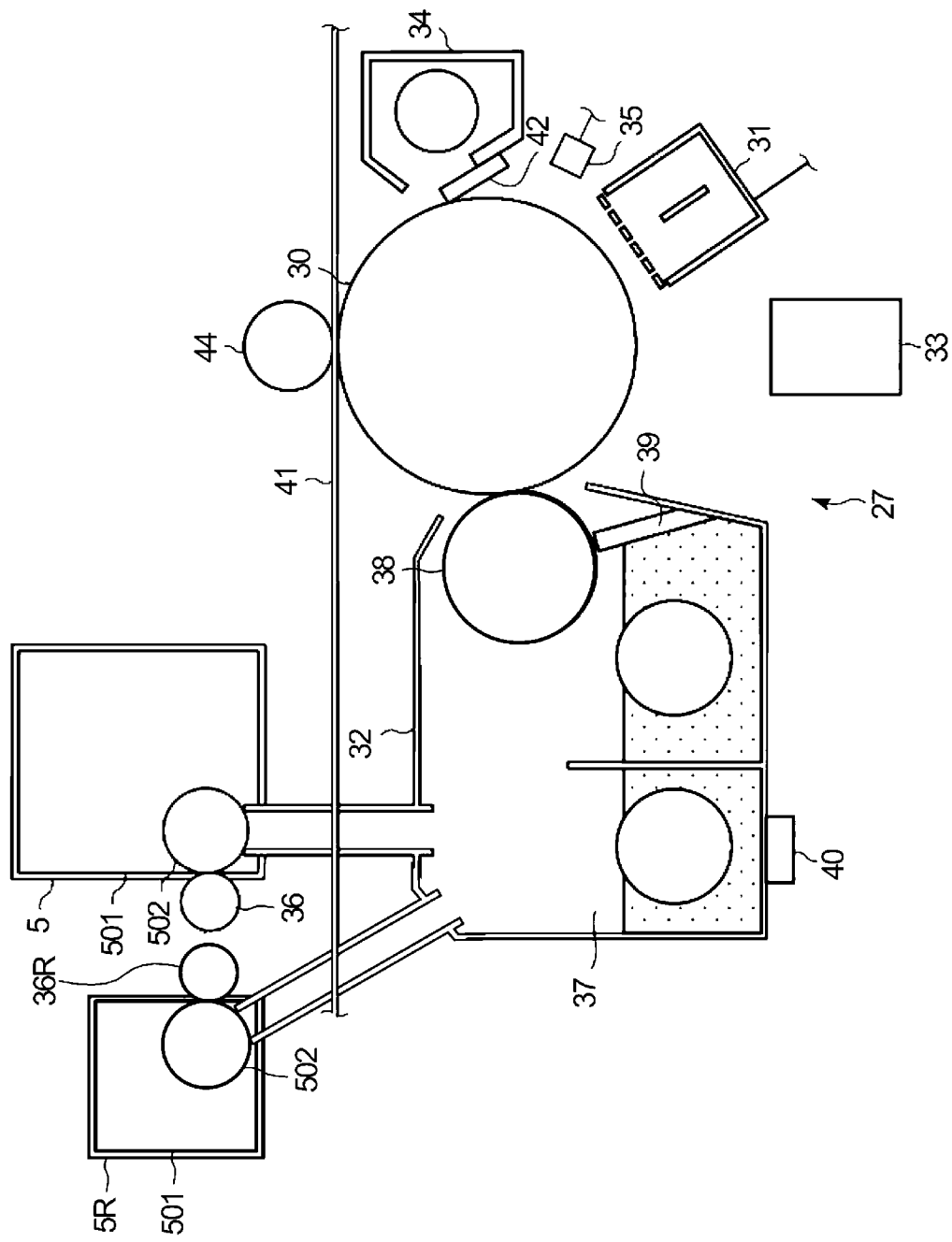
FIG. 3 is a diagram showing a configuration example of a process unit.

FIG. 3 is a diagram showing a configuration example of the process unit 27. The process unit 27 includes a photosensitive drum 30, a charging charger 31, and a developing device 32.

Further, the image forming unit 18 includes a plurality of exposure devices 33, a plurality of toner cleaners 34, a plurality of drum temperature sensors 35, a plurality of toner cartridge rotating motors 36, and a plurality of spare toner cartridge rotating motors 36R. The exposure device 33, the toner cleaner 34, the drum temperature sensor 35, the toner cartridge rotating motor 36, and the spare toner cartridge rotating motor 36R are provided for each process unit 27.

The photosensitive drum 30 is a photosensitive member including a cylindrical drum and a photosensitive layer formed on the outer peripheral surface of the drum. The photosensitive drum 30 is rotated at a constant speed by a drive mechanism including a photosensitive drum driving motor (not shown).

The charging charger 31 uniformly charges the surface of the photosensitive drum 30. For example, the charging charger 31 charges the photosensitive drum 30 to a uniform negative potential (contrast potential) by applying a voltage (developing bias voltage) to the photosensitive drum 30 using a charging roller. The charging roller is rotated by the rotation of the photosensitive drum 30 in a state where a predetermined pressure is applied to the photosensitive drum 30.

The developing device 32 is a device for adhering toner to the photosensitive drum 30. The developing device 32 includes a developer container 37, a developing roller 38, a doctor blade 39, an auto toner control sensor (ATC sensor) 40, and the like.

The developer container 37 is a container that stores a developer containing toner and a carrier. Toner is replenished from the toner cartridge 5 or the spare toner cartridge 5R. The developing roller 38 is rotated in the developer container 37 by a drive mechanism including a developing roller driving motor (not shown). Due to this rotation, the developing roller 38 carries the developer on its surface. The doctor blade 39 is a member disposed at a predetermined distance from the developing roller 38. The doctor blade 39 adjusts the thickness of the developer carried on the developing roller 38.

The ATC sensor 40 is, for example, a magnetic sensor having a coil and detecting a voltage value (ATC sensor detection voltage) generated in the coil. The ATC sensor 40 detects the toner density in the developer in the developer container 37 of the developing device 32. That is, the ATC sensor 40 detects the change in the magnetic flux accompanying the change in the toner density in the developer container 37 as the ATC sensor detection voltage generated in the coil. The ATC sensor 40 supplies the ATC sensor detection voltage to the system controller 13. The amount of toner in the developer container 37 is reflected in the ATC sensor detection voltage. That is, the system controller 13 can determine the density of the toner remaining in the developer container 37 based on the ATC sensor detection voltage and can perform the determination process of whether or not the toner replenishment is necessary. Toner is replenished from the toner cartridge 5 or the spare toner cartridge 5R to the developer container 37 based on the ATC sensor detection voltage.

The exposure device 33 includes, for example, a plurality of light emitting elements. The exposure device 33 forms a latent image on the photosensitive drum 30 by irradiating the photosensitive drum 30 with light from the light emitting element under the control of the system controller 13. The light emitting element is a light emitting diode (LED) or the like. One light emitting element is configured to irradiate one point on the photosensitive drum 30 with light. The plurality of light emitting elements are arranged in the main scanning direction, which is a direction parallel to the rotation axis of the photosensitive drum 30. The exposure device 33 forms a latent image for one line on the photosensitive drum 30 by irradiating the photosensitive drum 30 with light by the plurality of light emitting elements arranged in the main scanning direction. Further, the exposure device 33 forms a latent image by continuously irradiating the rotating photosensitive drum 30 with light.

The toner cleaner 34 removes the toner remaining on the photosensitive drum 30 after the toner image is transferred to the primary transfer belt 41, which is an intermediate transfer belt, which will be described later. The toner cleaner 34 has a blade 42 that comes into contact with the surface of the photosensitive drum 30. The toner cleaner 34 removes the toner remaining on the photosensitive drum 30 so as to peel off the toner from the surface of the photosensitive drum 30 by the blade 42.

The drum temperature sensor 35 is arranged in the vicinity of the photosensitive drum 30 and the developer container 37 and detects the atmospheric temperature of the surroundings including the photosensitive drum 30 and the developer container 37. The drum temperature sensor 35 supplies the temperature detection value to the system controller 13.

The toner cartridge rotating motor 36 rotates the screw of the toner cartridge 5 to supply toner from the toner cartridge 5 to the developing device 32. The toner cartridge rotating motor 36 rotates a drive mechanism (not shown). The drive mechanism is connected to a screw described later of the toner cartridge 5 if the toner cartridge 5 is mounted on the image forming apparatus 1. The screw rotates in conjunction with the rotation of the drive mechanism.

Similarly, the spare toner cartridge rotating motor 36R rotates the screw of the spare toner cartridge 5R to supply toner from the spare toner cartridge 5R to the developing device 32. The spare toner cartridge rotating motor 36R rotates a drive mechanism (not shown). The drive mechanism is connected to the screw described later of the spare toner cartridge 5R if the spare toner cartridge 5R is mounted on the image forming apparatus 1. The screw rotates in conjunction with the rotation of the drive mechanism.

In the above configuration, if the surface of the photosensitive drum 30 charged by the charging charger 31 is irradiated with light from the exposure device 33, an electrostatic latent image is formed. If the developer layer formed on the surface of the developing roller 38 is close to the photosensitive drum 30, the toner contained in the developer adheres to the latent image formed on the surface of the photosensitive drum. As a result, the process unit 27 forms a toner image on the surface of the photosensitive drum 30.

Further, according to the above configuration, the processor 21 of the system controller 13 calculates the toner density in the developer container 37 of the developing device 32 based on the preset reference value (ATC sensor reference value) and the output of the ATC sensor detection voltage supplied from the ATC sensor 40. Based on the calculated toner density, the processor 21 performs a toner replenishment necessity determination process for determining the necessity of replenishing the toner from the toner cartridge 5 or the spare toner cartridge 5R.

If the processor 21 determines in the toner replenishment necessity determination process that the amount of toner in the developer container 37 of the developing device 32 is decreasing, the operation of the toner cartridge rotating motor 36 or the spare toner cartridge rotating motor 36R is controlled to supply the toner from the toner cartridge 5 or the spare toner cartridge 5R to the developing device 32.

The transfer mechanism 28 has a configuration in which the toner image formed on the surface of the photosensitive drum 30 is transferred to the print medium P. The transfer mechanism 28 includes, for example, a primary transfer belt 41 which is an intermediate transfer belt, a secondary transfer opposed roller 43, a plurality of primary transfer rollers 44, and a secondary transfer roller 45.

The primary transfer belt 41 is an endless belt wound around the secondary transfer opposed roller 43 and a plurality of driven rollers. In the primary transfer belt 41, the inner surface (inner peripheral surface) is in contact with the secondary transfer opposed roller 43 and the plurality of driven rollers, and the outer surface (outer peripheral surface) faces the photosensitive drum 30 of the process unit 27.

The secondary transfer opposed roller 43 is rotated by a motor (not shown). The secondary transfer opposed roller 43 rotates to transfer the primary transfer belt 41 in a predetermined conveyance direction. The plurality of driven rollers are configured to be freely rotatable. The plurality of driven rollers rotate according to the movement of the primary transfer belt 41 by the secondary transfer opposed roller 43.

The plurality of primary transfer rollers 44 have a configuration in which the primary transfer belt 41 is brought into contact with the photosensitive drum 30 of the process unit 27. The plurality of primary transfer rollers 44 are provided so as to correspond to the photosensitive drums 30 of the plurality of process units 27. Specifically, the plurality of primary transfer rollers 44 are provided at positions facing each other with the photosensitive drum 30 of the corresponding process unit 27 and the primary transfer belt 41 interposed therebetween. The primary transfer roller 44 comes into contact with the inner peripheral surface side of the primary transfer belt 41 and displaces the primary transfer belt 41 toward the photosensitive drum 30 side. As a result, the primary transfer roller 44 brings the outer peripheral surface of the primary transfer belt 41 into contact with the photosensitive drum 30.

The secondary transfer roller 45 is provided at a position facing the secondary transfer opposed roller 43 with the primary transfer belt 41 interposed therebetween. The secondary transfer roller 45 comes into contact with the outer peripheral surface of the primary transfer belt 41 and applies pressure. As a result, a transfer nip is formed in which the secondary transfer roller 45 and the outer peripheral surface of the primary transfer belt 41 are in close contact with each other. If the print medium P passes through the transfer nip, the secondary transfer roller 45 presses the print medium P passing through the transfer nip against the outer peripheral surface of the primary transfer belt 41.

The secondary transfer roller 45 and the secondary transfer opposed roller 43 rotate to convey the print medium P supplied from the paper feed conveyance path 24 in a sandwiched state. As a result, the print medium P passes through the transfer nip.

The toner image formed on the surface of the photosensitive drum 30 is transferred to the outer peripheral surface of the primary transfer belt 41. If the image forming unit 18 includes the plurality of process units 27, the primary transfer belt 41 receives the toner image from the photosensitive drums 30 of the plurality of process units 27. The toner image transferred to the outer peripheral surface of the primary transfer belt 41 is conveyed by the primary transfer belt 41 to the transfer nip in which the secondary transfer roller 45 and the outer peripheral surface of the primary transfer belt 41 are in close contact with each other. If the print medium P is present in the transfer nip, the toner image transferred to the outer peripheral surface of the primary transfer belt 41 is transferred to the print medium P in the transfer nip.

The processor 21 forms toner pattern images having different densities on the primary transfer belt 41 for each toner by each process unit 27. A density sensor (not shown) detects the density of the toner pattern image, and the processor 21 can adjust the image formation conditions based on the detection result.

The temperature and humidity sensor 29 measures the entire atmospheric temperature and atmospheric humidity in the image forming unit 18. The temperature and humidity sensor 29 is arranged between the process unit 27 arranged at the most downstream in the sub-scanning direction, which is a direction orthogonal to the main scanning direction of the image forming unit 18 and the transfer nip. The temperature and humidity sensor 29 supplies the detected values of temperature and humidity to the system controller 13. The temperature and humidity sensor 29 may be arranged at different positions in the sub-scanning direction. Further, the temperature and humidity sensor 29 may be arranged in the vicinity of each of the plurality of process units 27 to measure the atmospheric temperature and the atmospheric humidity around each process unit 27. A temperature sensor may be used instead of the temperature and humidity sensor 29.

Next, the configuration related to the fixing of the image forming apparatus 1 will be described. The fixing device 19 fixes the toner image on the print medium P on which the toner image was transferred. The fixing device 19 operates under the control of the system controller 13. The fixing device 19 includes a heating member that applies heat to the print medium P and a pressurizing member that applies pressure to the print medium P. For example, the heating member is a heat roller 46. Further, for example, the pressurizing member is a press roller 47.

The heat roller 46 is a fixing rotating body that is rotated by a drive mechanism including a heat roller motor (not shown). The heat roller 46 includes a core metal formed of hollow metal and an elastic layer formed on the outer periphery of the core metal. The heat roller 46 is heated to a high temperature by a heater arranged inside the hollow core metal. The heater is, for example, a halogen heater. Further, the heater may be an induction heating (IH) heater that heats the core metal by electromagnetic induction.

The press roller 47 is provided at a position facing the heat roller 46. The press roller 47 includes a core metal formed of metal with a predetermined outer diameter and an elastic layer formed on the outer periphery of the core metal. The press roller 47 applies pressure to the heat roller 46 by the stress applied from a tension member (not shown). If pressure is applied from the press roller 47 to the heat roller 46, a nip in which the press roller 47 and the heat roller 46 are in close contact, that is, a so-called fixing nip is formed. The press roller 47 is rotated by a motor (not shown). The press roller 47 rotates to move the print medium P that entered the fixing nip and presses the print medium P against the heat roller 46.

With the above configuration, the heat roller 46 and the press roller 47 apply heat and pressure to the print medium P passing through the fixing nip. As a result, the toner image is fixed on the print medium P that passed through the fixing nip. The print medium P that passed through the fixing nip is introduced into the paper discharge conveyance path 25 and discharged to the outside of the housing 10.

Next, the configurations of the toner cartridge 5 and the spare toner cartridge 5R will be described. The toner cartridge 5 includes the toner cartridge 5C containing cyan toner, the toner cartridge 5M containing magenta toner, the toner cartridge 5Y containing yellow toner, and the toner cartridge 5K containing black toner. Similarly, the spare toner cartridge 5R contains the spare toner cartridge 5CR containing cyan toner, the spare toner cartridge 5MR containing magenta toner, the spare toner cartridge 5YR containing yellow toner, and the spare toner cartridge 5KR containing black toner.

As shown in FIG. 3, the toner cartridge 5 includes a storage container 501 and a screw 502. Further, the spare toner cartridge 5R also includes the same hardware configuration as the toner cartridge 5. Here, the toner cartridge 5 will be described.

The storage container 501 is connected to the developer container 37 of the developing device 32 if the toner cartridge 5 is mounted on the image forming apparatus 1.

The screw 502 is a delivery mechanism that is provided in the storage container 501 and sends out the toner in the storage container 501 to the developing device 32 by rotating. The screw 502 is driven by the toner cartridge rotating motor 36 of the process unit 27.

The infrared thermography camera 20 is oriented in the direction of detecting the operator and is equipped at a position where the body surface temperature of the operator of the housing 10 can be measured. The output of the infrared thermography camera 20 is input to the system controller 13, and the processor 21 of the system controller 13 determines the body surface temperature of the operator based on the output of the infrared thermography camera 20.

Next, the operation unit 14 will be described. The operation unit 14 is configured to be able to switch between a touch panel state, which is a state if the operator is a person without a fever, and an aerial touch panel state, which is a state if the operator is a person with a fever.

Figure 4:
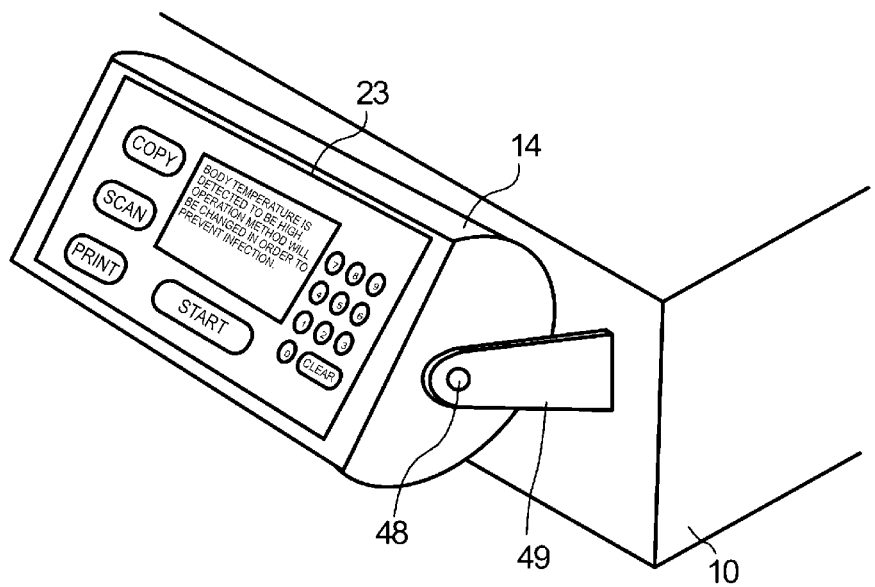
FIG. 4 is a perspective view showing an example of a touch panel state of an operation unit.
Figure 5:
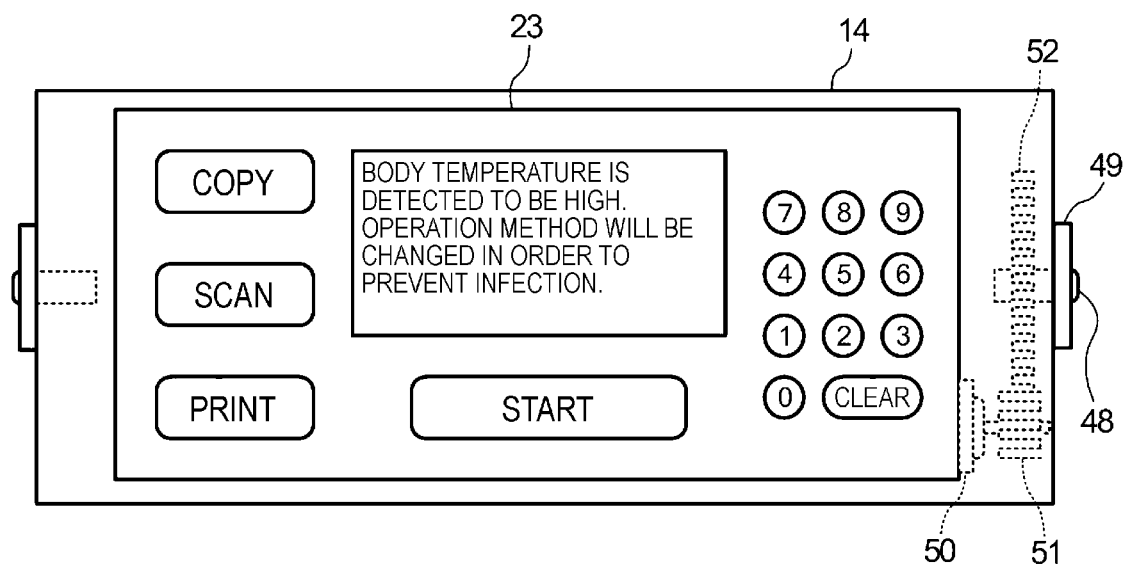
FIG. 5 is a front view of the operation unit in the touch panel state.

FIG. 4 is a perspective view showing an example of the touch panel state of the operation unit 14, and FIG. 5 is a front view of the operation unit 14 in the touch panel state. The operation unit 14 is supported by a support arm 49 extending from the housing 10 so as to be rotatable around a rotary shaft 48 fixed to the operation unit 14. If the operator is a person without a fever, the liquid crystal touch panel 23 is arranged on one surface of the operation unit 14 so that the liquid crystal touch panel 23 faces the operator. The liquid crystal display constituting the liquid crystal touch panel 23 can display various button images for the operator to perform a touch operation, input contents corresponding to the operator's touch operation, a message to be presented to the operator, and the like.

Figure 6:
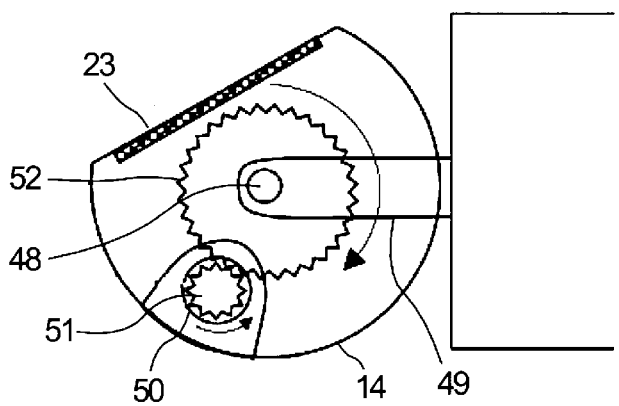
FIG. 6 is a schematic diagram showing a state before rotation of the operation unit.
Figure 7:
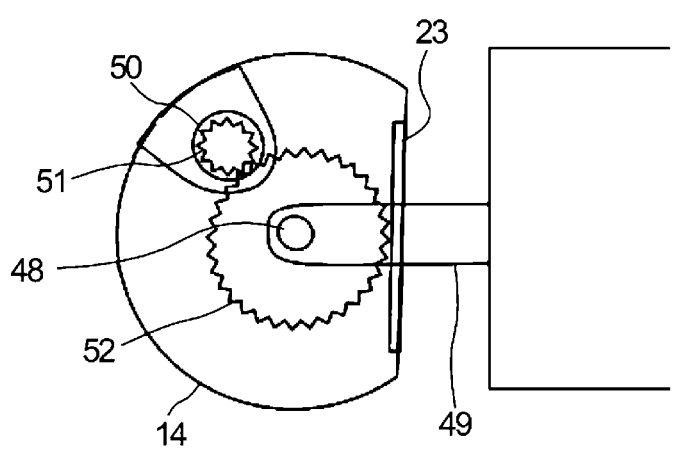
FIG. 7 is a schematic diagram showing a state after rotation of the operation unit.

Inside the operation unit 14, a rotation mechanism for rotating the operation unit 14 is provided. The rotation mechanism includes an operation unit rotating motor 50, a first rotary gear 51, and a second rotary gear 52. FIG. 6 is a schematic diagram showing a state before rotation of the operation unit 14, and FIG. 7 is a schematic diagram showing a state after rotation likewise. The operation unit rotating motor 50 is fixed inside the operation unit 14, and the first rotary gear 51 is fixed to the rotation shaft of the operation unit rotating motor 50. Further, the second rotary gear 52 is fixed to the rotary shaft 48 inside the operation unit 14. The first rotary gear 51 and the second rotary gear 52 are in mesh with each other.

Therefore, if the rotary shaft of the operation unit rotating motor 50, that is, the first rotary gear 51 rotates as shown by an arrow in FIG. 6, the second rotary gear 52 meshed with the first rotary gear 51 rotates in the opposite direction to that of the first rotary gear 51. Along with the rotation of the second rotary gear 52, the rotary shaft 48 rotates, and as a result, the operation unit 14 itself rotates. As shown in FIG. 7, this rotation is continued until the liquid crystal touch panel 23 faces the housing 10.

Figure 8:
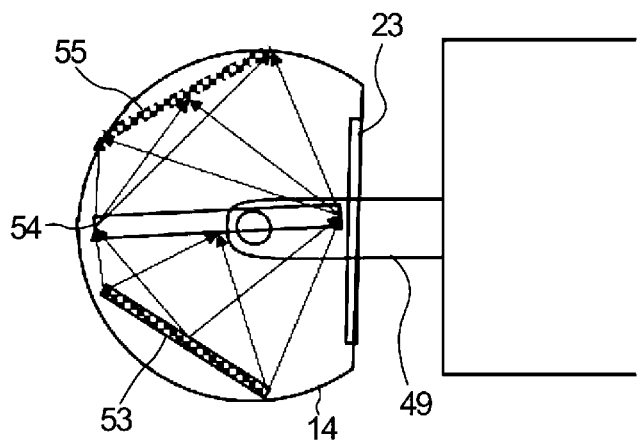
FIG. 8 is a schematic diagram for illustrating the projection of an aerial touch panel on the operation unit.
Figure 9:
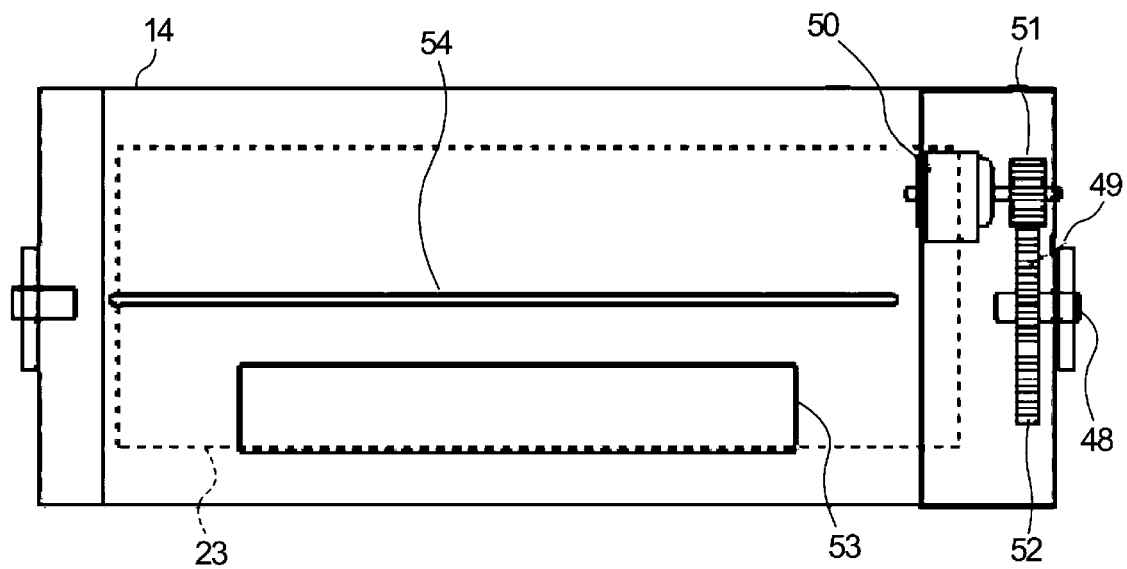
FIG. 9 is a front view showing an example of an aerial touch panel state of the operation unit.
Figure 10:
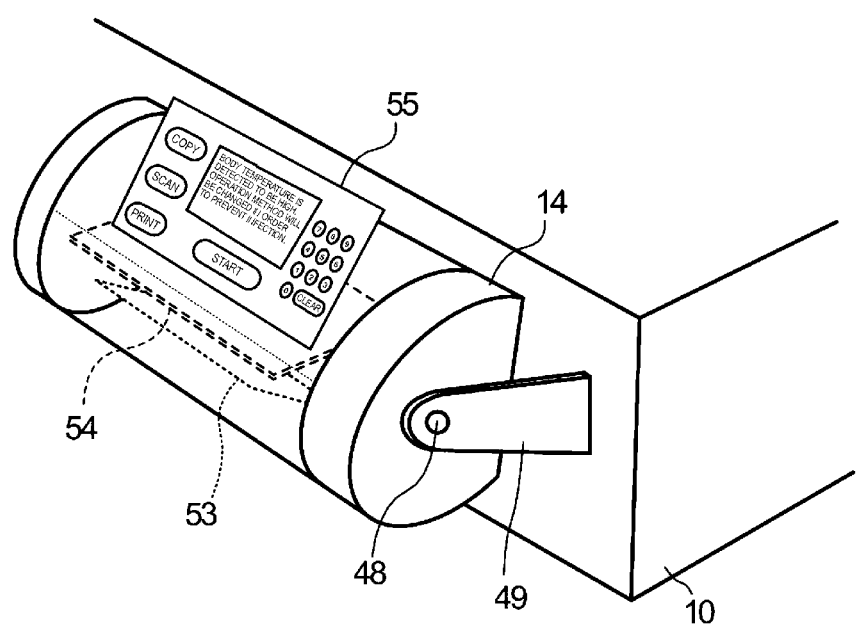
FIG. 10 is a perspective view of the operation unit in an aerial touch panel state.

FIG. 8 is a schematic diagram for illustrating the projection of the aerial touch panel on the operation unit 14, and FIG. 9 is a front view showing an example of the aerial touch panel state of the operation unit 14. Further, FIG. 10 is a perspective view of the operation unit 14 in the aerial touch panel state. Inside the operation unit 14, an aerial liquid crystal display 53 for implementing an aerial touch panel, an aerial touch panel 3 D plate 54, an aerial touch detection sensor (not shown), and the like are arranged. As shown by the arrows in FIG. 8, the image projected on the aerial liquid crystal display 53 is polarized through the aerial touch panel 3D plate 54 in the middle and imaged on the target surface to be projected as a display floating in the air. That is, an aerial touch panel projection image 55 facing the operator is formed on the operation unit 14. For example, an aerial touch detection sensor made of an ultrasonic sensor detects where the operator touches on the aerial touch panel projection image 55. This enables display and touch position detection equivalent to those of the liquid crystal touch panel 23. The aerial touch detection sensor may be, for example, a two-dimensional infrared camera disclosed in U.S. Pat. No. 10,019,115 B2, an optical sensor two-dimensionally arranged on the display surface disclosed in US 2018/0011605 A1, and the like.

As described above, in the operation unit 14, the operation unit rotating motor 50 rotates from the touch panel state in which the liquid crystal touch panel 23, which is of a contact input method, is on the front side, so that the operation unit 14 itself is rotated by the first rotary gear 51 and the second rotary gear 52 and the liquid crystal touch panel 23 is rotated to the back side. Thereby, the operation unit 14 can put the operation surface into the aerial touch panel state in which the aerial touch panel projection image 55 that implements the non-contact input method appears on the front side. Further, in the operation unit 14, the operation unit rotating motor 50 rotates in the reverse direction from the aerial touch panel state, so that the operation unit 14 itself is rotated in the reverse direction by the first rotary gear 51 and the second rotary gear 52 and the liquid crystal touch panel 23 can be returned to the front side. The operation unit 14 is not limited to such a rotation configuration. For example, the configuration can be any configuration such as that the liquid crystal touch panel 23 evacuates from the front of the operation unit 14 to form the aerial touch panel projection image 55 in the vacant space, or the evacuated liquid crystal touch panel 23 can be used as the aerial liquid crystal display 53.

Figure 11:
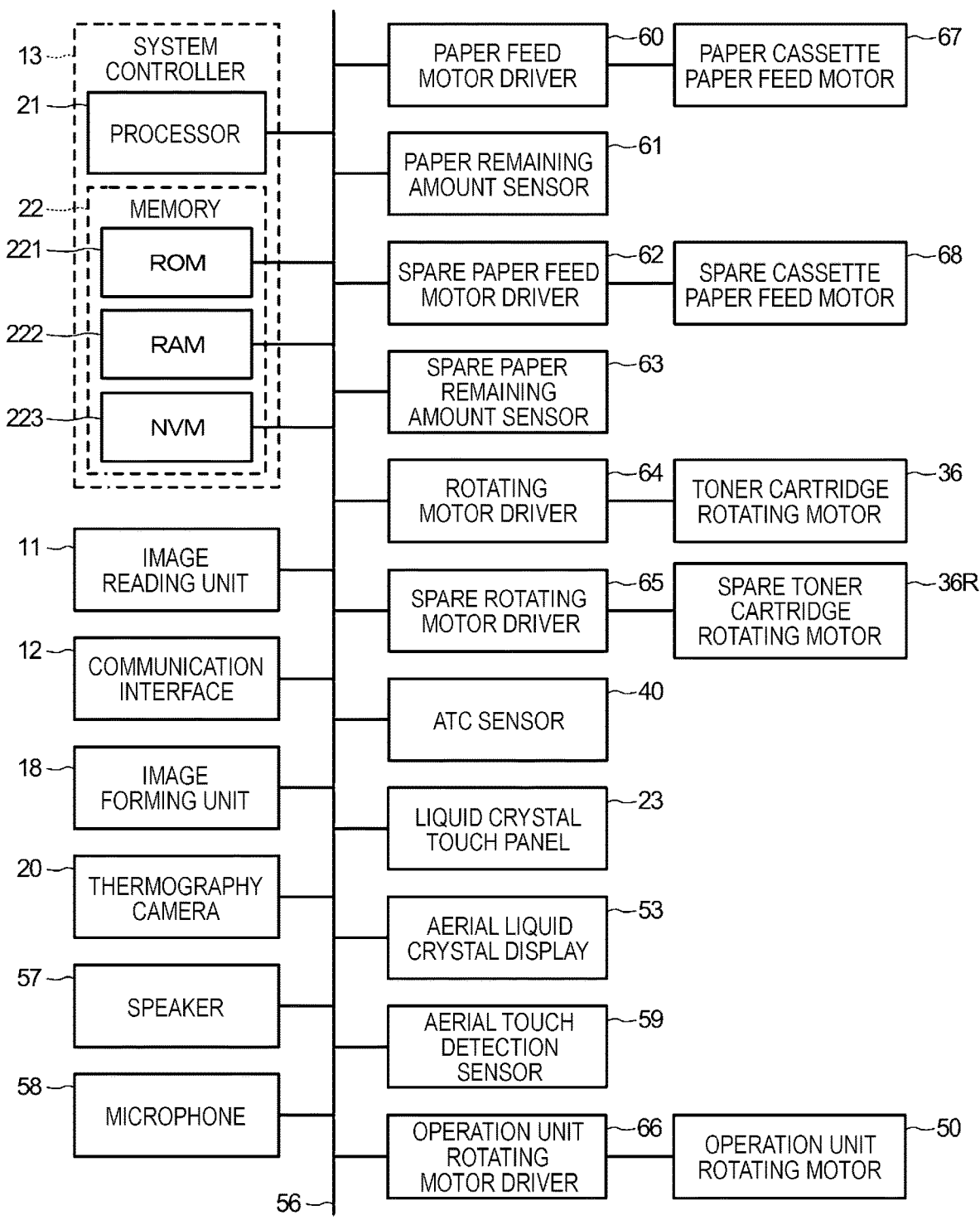
FIG. 11 is a block diagram showing an example of an electrical configuration of the image forming apparatus.

Next, the electrical configuration of the image forming apparatus 1 will be described. FIG. 11 is a block diagram showing an example of an electrical configuration of the image forming apparatus 1. As described above, the system controller 13 includes the processor 21 and the memory 22.

The memory 22 includes a ROM 221 which is a program memory, a RAM 222 used by the processor 21 as a work memory, a non-volatile memory (NVM) 223 which stores various control parameters even if the image forming apparatus 1 is not turned on, and the like. The NVM. 223 can store administrator contact information such as the network address of the administrator terminal 4 and the email address of the administrator, for example.

The processor 21 is connected to the ROM 221, the RAM 222, and the NVM 223 of the memory 22 via a bus 56.

The RAM 222 as a work memory stores an image signal generated by the image reading unit 11 or image data from the communication interface 12. The processor 21 performs predetermined image processing in order to convert the image signals or image data stored in the RAM 222 into image data suitable for image formation by the image forming unit 18. The predetermined processing includes, for example, for the output image (printout), processing, for example, such as character identification, contour correction, color tone correction (color conversion, RGB→CMY, density), halftone (gradation), γ characteristic (input density value to output density). The image signal and image data that have undergone image processing can be stored in the NVM 223 or a storage device (not shown), for example, a hard disk drive (HDD). Further, the image signal and the image data can be stored in a semiconductor memory (not shown) that can be taken out from the image forming apparatus 1. In addition to the processor 21, the system controller 13 may include an image processing unit including a CPU that exclusively performs such image processing.

The processor 21 further converts the image data that has undergone image processing into a modulated signal, that is, an exposure signal for use as exposure light by each exposure device 33, and supplies the image data to the image forming unit 18. Therefore, the processor 21 is connected to the image forming unit 18 via the bus 56.

Further, the processor 21 accesses the image reading unit 11, the communication interface 12, the infrared thermography camera 20, the liquid crystal touch panel 23, the ATC sensor 40 of each process unit 27, and the aerial liquid crystal display 53 via the bus 56. In FIG. 11, the "infrared thermography camera" is abbreviated as "thermography camera".

Further, the processor 21 is connected to a speaker 57, an audio input microphone 58, an aerial touch detection sensor 59, a paper cassette paper feed motor driver 60, a paper cassette remaining amount detection sensor 61, a spare paper cassette paper feed motor driver 62, a spare paper cassette remaining amount detection sensor 63, a toner cartridge rotating motor driver 64, a spare toner cartridge rotating motor driver 65, and an operation unit rotating motor driver 66 via the bus 56. In FIG. 11, the "audio input microphone" is referred to as "microphone", the "paper cassette paper feed motor driver" is referred to as "paper feed motor driver", the "paper cassette remaining amount detection sensor" is referred to as "paper remaining amount sensor", the "spare paper cassette paper feed motor driver" is referred to as "spare paper feed motor driver", the "spare paper cassette remaining amount detection sensor" is referred to as "spare paper remaining amount sensor", the "toner cartridge rotating motor driver" is referred to as "rotating motor driver", and the "spare toner cartridge rotating motor driver" is referred to as "spare rotating motor driver".

The speaker 57 outputs an operation sound and outputs various voice messages. That is, the processor 21 can not only display the message on the liquid crystal touch panel 23 or the aerial touch panel projection image 55 but also present the message to the operator by audio from the speaker 57.

The audio input microphone 58 acquires the voice of the operator. The processor 21 can receive the operation control of the image forming apparatus 1 by the voice instruction of the operator by recognizing the voice acquired by the audio input microphone 58. Therefore, in the case of a person with a fever, it is also possible to configure only the aerial touch panel projection image 55 instead of the aerial touch panel to be switched and to accept an operation instruction by voice without detecting the aerial touch operation of the operator.

The aerial touch detection sensor 59 detects where on the aerial touch panel projection image 55 the operator touches. The processor 21 can determine the operation instruction content of the operator based on the image position of the operation button or the like displayed on the aerial touch panel projection image 55 and the position detected by the aerial touch detection sensor 59.

A paper cassette paper feed motor 67 is connected to the paper cassette paper feed motor driver 60. The paper cassette paper feed motor driver 60 controls the rotation of the paper cassette paper feed motor 67 according to the instructions of the processor 21. The paper cassette paper feed motor 67 rotates the pickup roller 26 corresponding to the paper cassette 15 to pick up the paper, that is, the print medium P contained in the paper cassette 15 into the paper feed conveyance path 24.

The paper cassette remaining amount detection sensor 61 detects the remaining amount of the print medium P contained in the paper cassette 15. Based on the detection result of the paper cassette remaining amount detection sensor 61, the processor 21 can determine whether or not the print medium P contained in the paper cassette 15 was used up, that is, whether or not the paper cassette 15 needs to be replenished with the print medium P.

A spare paper cassette paper feed motor 68 is connected to the spare paper cassette paper feed motor driver 62. The spare paper cassette paper feed motor driver 62 controls the rotation of the spare paper cassette paper feed motor 68 according to the instructions of the processor 21. The spare paper cassette paper feed motor 68 rotates the pickup roller 26 corresponding to the spare paper cassette 15R and introduces the paper, that is, the print medium P contained in the spare paper cassette 15R into the paper feed conveyance path 24.

The spare paper cassette remaining amount detection sensor 63 detects the remaining amount of the print medium P contained in the spare paper cassette 15R. Based on the detection result of the spare paper cassette remaining amount detection sensor 63, the processor 21 can determine whether or not the print medium P contained in the spare paper cassette 15R was used up, that is, whether or not the spare paper cassette 15R needs to be replenished with the print medium P.

The toner cartridge rotating motor 36 described above is connected to the toner cartridge rotating motor driver 64. The toner cartridge rotating motor driver 64 controls the rotation of the toner cartridge rotating motor 36 according to the instructions of the processor 21. The toner cartridge rotating motor 36 rotates a screw 502 provided in the storage container 501 of the toner cartridge 5 to send out the toner in the storage container 501 to the developing device 32.

The spare toner cartridge rotating motor 36R described above is connected to the spare toner cartridge rotating motor driver 65. The spare toner cartridge rotating motor driver 65 controls the rotation of the spare toner cartridge rotating motor 36R according to the instruction of the processor 21. The spare toner cartridge rotating motor 36R rotates the screw 502 provided in the storage container 501 of the spare toner cartridge 5R and sends out the toner in the storage container 501 to the developing device 32.

The processor 21 controls the toner cartridge rotating motor 36 by the toner cartridge rotating motor driver 64 or controls the spare toner cartridge rotating motor 36R by the spare toner cartridge rotating motor driver 65 to supply toner to the developing device 32 from the toner cartridge 5 or the spare toner cartridge 5R. Then, the processor 21 can detect the occurrence of toner shortage in the toner cartridge 5 or the spare toner cartridge 5R depending on the presence or absence of the output change of the ATC sensor 40 at that time. The processor 21 can determine whether or not the toner cartridge 5 or the spare toner cartridge 5R needs to be replaced based on whether or not the toner shortage occurred in the toner cartridge 5 or the spare toner cartridge 5R.

The operation unit rotating motor 50 described above is connected to the operation unit rotating motor driver 66. The operation unit rotating motor driver 66 controls the rotation of the operation unit rotating motor 50 according to the instruction of the processor 21. The operation unit rotating motor 50 rotates the operation unit 14 itself by the first rotary gear 51 and the second rotary gear 52, and switches between the liquid crystal touch panel 23, which is of a contact input method, and the aerial touch panel projection image 55, which implements a non-contact input method, as an operation surface facing the operator.

The operation of the image forming apparatus 1 will be described below. The contents of the process described below are examples, and various processes capable of obtaining similar results can be appropriately used.

Figure 12:
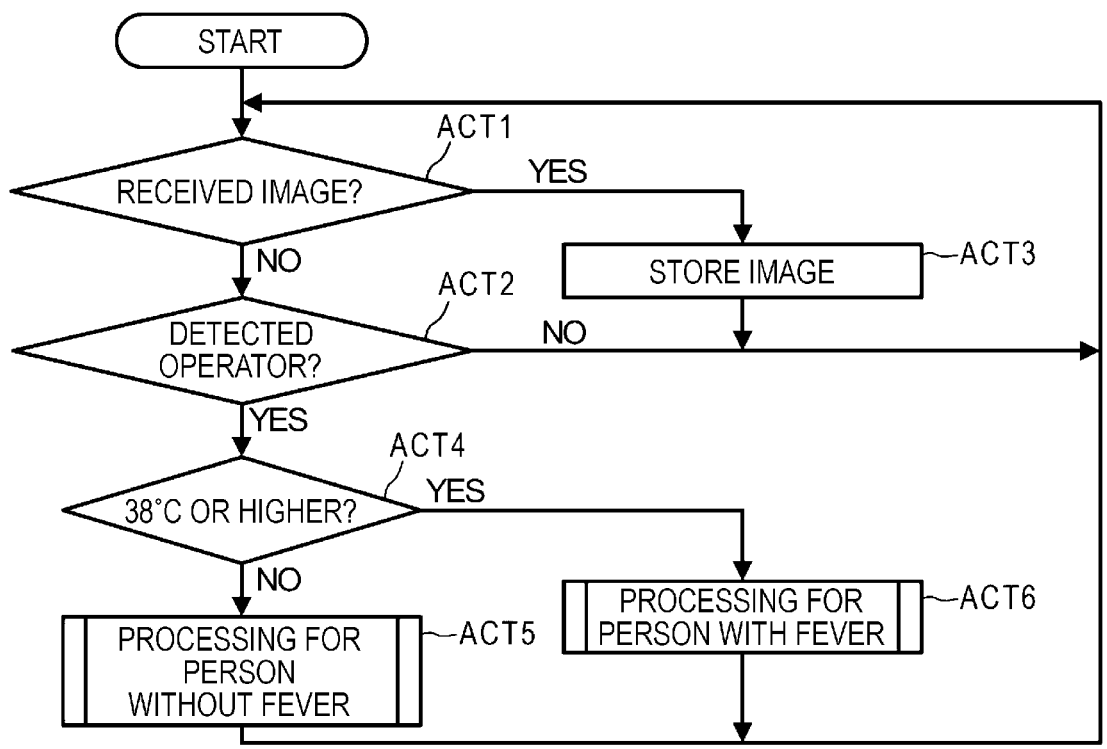
FIG. 12 is a flowchart showing an example of operation processing of the image forming apparatus.

FIG. 12 is a flowchart showing an example of the operation processing of the image forming apparatus 1 according to an embodiment. The processor 21 performs the control process shown in FIG. 12 according to the control program stored in the ROM 221.

If the power of the image forming apparatus 1 is turned on, the processor 21 determines whether the image data from the user terminal 2 via the communication interface 12 was received after performing initial settings such as preheating of the image forming unit 18 and the fixing device 19 (ACT 1). If it is determined that the image data was not received (ACT 1, NO), the processor 21 determines whether or not an operator is detected, that is, an operator is in front of the image forming apparatus 1, based on the output of the infrared thermography camera 20 (ACT 2). If it is determined that no operator is detected (ACT 2, NO), the processor 21 shifts to the process of ACT 1.

If it is determined that the image data was received (ACT 1, YES), the processor 21 stores the image data in the RAM 222 (ACT 3). After that, the processor 21 shifts to the process of ACT 1.

If it is determined that an operator is detected (ACT 2, YES), the processor 21 determines whether or not the body surface temperature of the operator is equal to or higher than a threshold temperature, 38° C. or higher in the present embodiment, based on the output of the infrared thermography camera 20 (ACT 4). If it is determined that the body surface temperature of the operator is less than 38° C. (ACT 4, NO), the processor 21 forms an image on the print medium P by a subroutine of processing for a person without a fever as described later (ACT 5). After that, the processor 21 shifts to the process of ACT 1.

Further, if it is determined that the body surface temperature of the operator is 38° C. or higher (ACT 4, YES), the processor 21 forms an image on the print medium P by a subroutine of processing for a person with a fever as described later (ACT 6). After that, the processor 21 shifts to the process of ACT 1.

Figure 13:
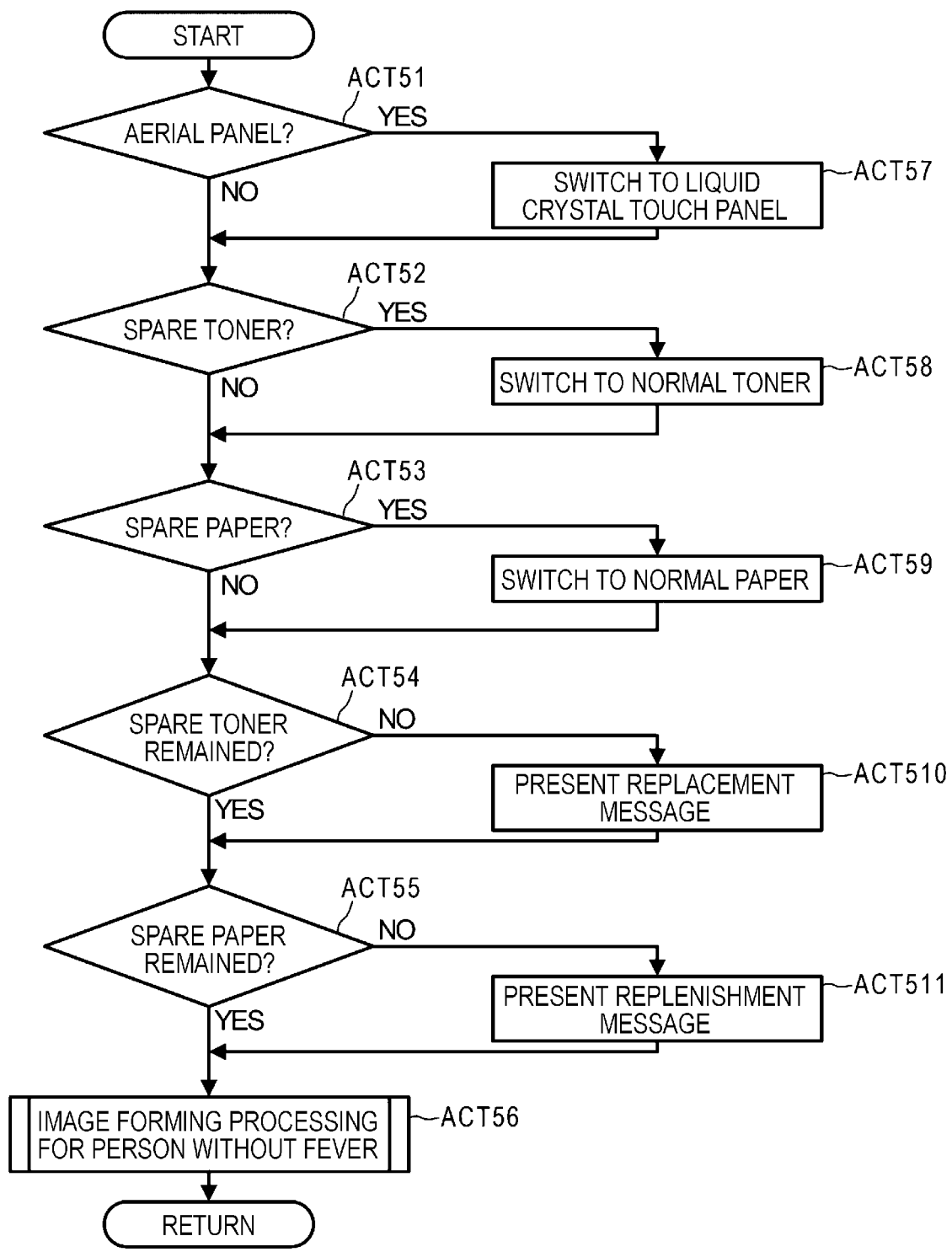
FIG. 13 is a flowchart showing an example of a subroutine of processing for a person without a fever processing in FIG. 12.

FIG. 13 is a flowchart showing an example of the subroutine of processing for a person without a fever of ACT 5. The processor 21 determines whether or not the operation unit 14 is in the aerial touch panel state in which the aerial touch panel projection image 55 is on the front side (ACT 51). If another operator who used the image forming apparatus 1 immediately before the operator, that is, the previous operator is a person with a fever, the operation unit 14 is in the aerial touch panel state.

If it is determined that the operation unit 14 is not in the aerial touch panel state (ACT 51, NO), the processor 21 determines whether or not the toner cartridge was switched to the spare toner cartridge 5R (ACT 52). If the previous operator was a person with a fever and there is no remaining amount of toner in the toner cartridge 5, the toner cartridge was switched to the spare toner cartridge 5R. Even if the previous operator was a person with a fever, if there was a remaining amount of toner in the toner cartridge 5, the toner cartridge was not switched to the spare toner cartridge 5R.

If it is determined that the toner cartridge was not switched to the spare toner cartridge 5R (ACT 52, NO), the processor 21 determines whether or not the paper cassette was switched to the spare paper cassette 15R (ACT 53). If the previous operator was a person with a fever and there was no print medium P of the paper cassette 15, the paper cassette was switched to the spare paper cassette 15R. Even if the previous operator was a person with a fever, if the print medium P contained in the paper cassette 15 remained, the paper cassette 15 was not switched to the spare paper cassette 15R.

If it is determined that the paper cassette was not switched to the spare paper cassette 15R (ACT 53, NO), the processor 21 determines whether or not there is a remaining amount of spare toner contained in the spare toner cartridge 5R (ACT 54). Therefore, if the processor 21 determines the remaining amount of toner in the spare toner cartridge 5R in the subroutine of processing for a person with a fever described later, the determination result is stored in the NVM 223, and this determination result is used in the process of ACT 54. Alternatively, the processor 21 may temporarily switch the toner cartridge to the spare toner cartridge 5R, determine the remaining amount of spare toner in the spare toner cartridge 5R based on the output of the ATC sensor 40, and return to the toner cartridge 5 after the determination is completed.

If it is determined that there is a remaining amount of the spare toner in the spare toner cartridge 5R (ACT 54, YES), the processor 21 determines whether or not the spare print medium P which is the spare paper contained in the spare paper cassette 15R is remained (ACT 55).

If it is determined that there is spare paper in the spare paper cassette 15R (ACT 55, YES), the processor 21 actually forms an image on the print medium P by a subroutine of image forming processing for a person without a fever as described later (ACT 56). After that, the processor 21 ends the subroutine of processing for a person without a fever and shifts to the process of ACT 1.

If it is determined that the operation unit is in the aerial touch panel state (ACT 51, YES), the processor 21 controls the operation unit rotating motor 50 by the operation unit rotating motor driver 66 to rotate and switch the operation unit 14 to the touch panel state in which the liquid crystal touch panel 23 is on the front side (ACT 57). After that, the processor 21 shifts to the process of ACT 52.

If it is determined that the toner cartridge was switched to the spare toner cartridge 5R (ACT 52, YES), the processor 21 switches to the normal toner cartridge 5 (ACT 58). After that, the processor 21 shifts to the process of ACT 53.

If it is determined that the paper cassette was switched to the spare paper cassette 15R (ACT 53, YES), the processor 21 switches to the normal paper cassette 15 (ACT 59). After that, the processor 21 shifts to the process of ACT 54.

If it is determined that there is no remaining amount of the spare toner in the spare toner cartridge 5R (ACT 54, NO), the processor 21 presents a replacement message requesting replacement of the spare toner cartridge 5R to the operator (ACT 510). For example, the processor 21 may display a replacement message such as "The spare toner has run out. Please replace it with a new toner cartridge." on the liquid crystal touch panel 23 of the operation unit 14, or cause the speaker 57 to output such a replacement message in audio. After that, the processor 21 shifts to the process of ACT 55. It is not essential for the operator to replace the spare toner cartridge 5R in response to this replacement message, and therefore, the processor does not determine or wait for the replacement here.

Further, if it is determined that there is no spare paper in the spare paper cassette 15R (ACT 55, NO), the processor 21 presents, to the operator, a replenishment message requesting the replenishment of the print medium P to the spare paper cassette 15R (ACT 511). For example, the processor 21 may display a replenishment message such as "There is no paper in the spare cassette. Please replenish the paper." on the liquid crystal touch panel 23 of the operation unit 14, or cause the speaker 57 to output such a replenishment message in audio. After that, the processor 21 shifts to the process of ACT 56. It is not essential for the operator to replenish the print medium P to the spare paper cassette 15R in response to this replenishment message, and therefore, the processor does not determine or wait for the replenishment here.

Figure 14:
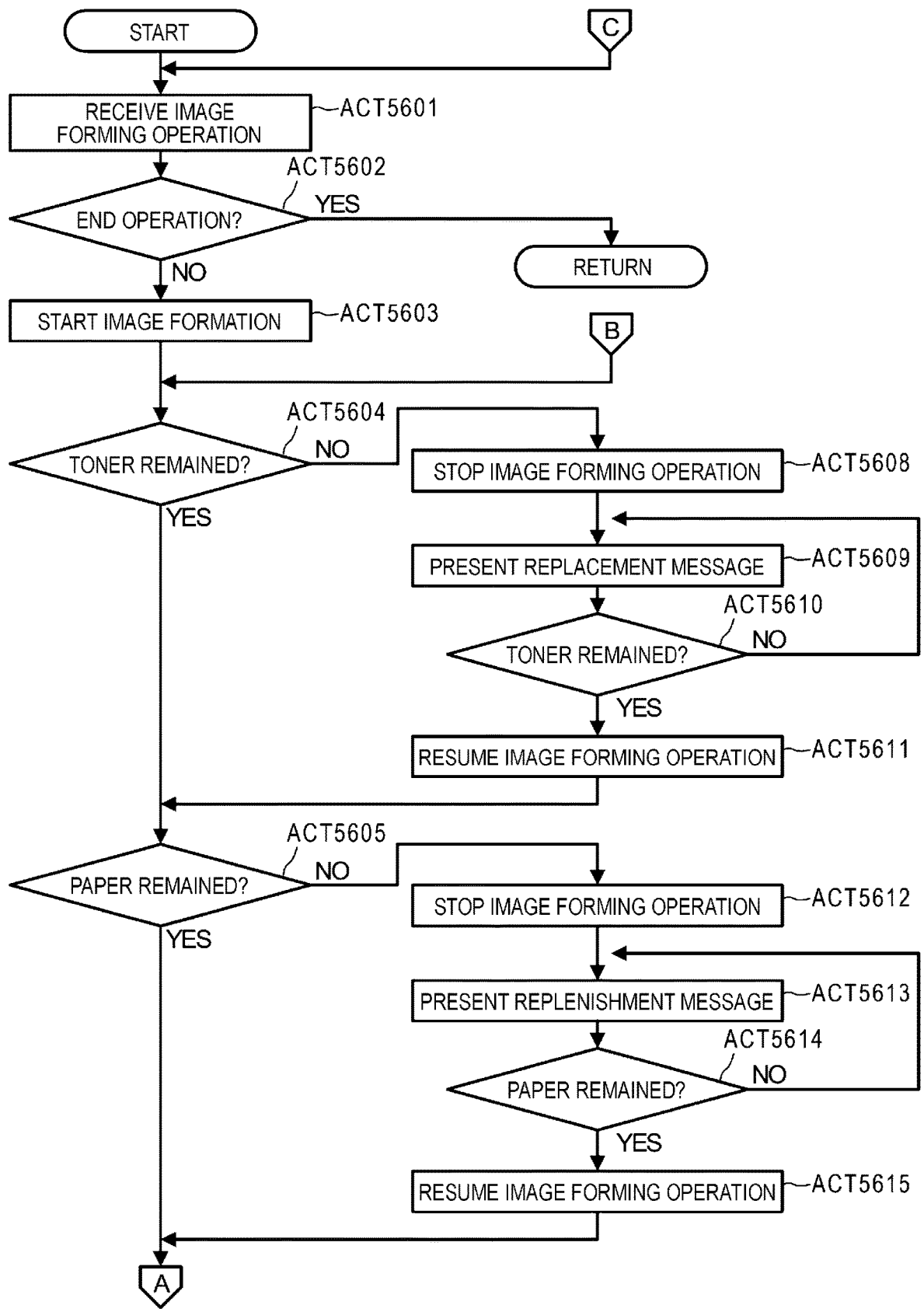
FIG. 14 is a flowchart showing an example of a subroutine of the image forming processing for a person without a fever in FIG. 13.
Figure 15:
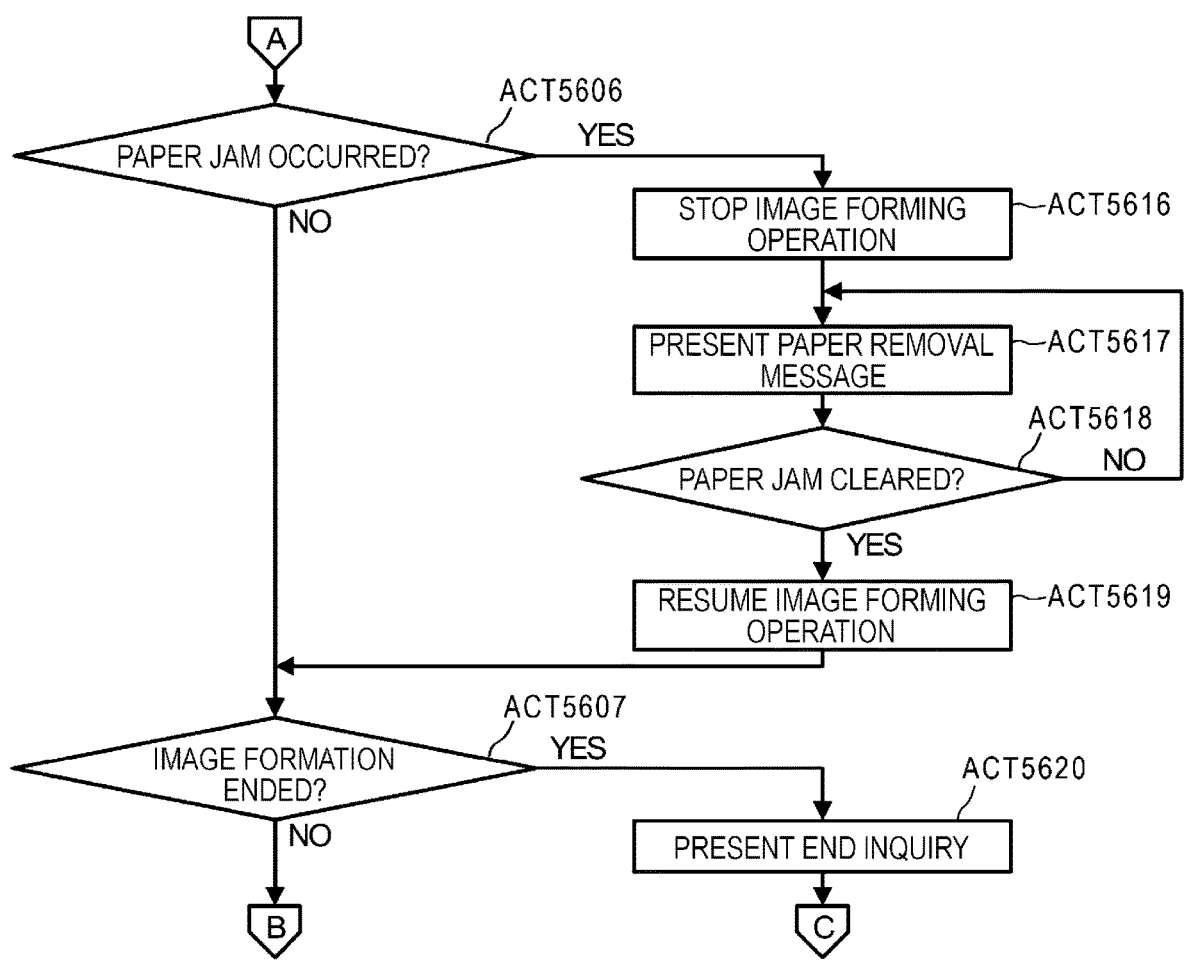
FIG. 15 is a flowchart showing an example of a subroutine of the image forming processing for a person without a fever in FIG. 13.

FIGS. 14 and 15 are flowcharts showing an example of the subroutine of the image forming processing for a person without a fever of ACT 56. First, the processor 21 accepts an image forming operation from the liquid crystal touch panel 23 by an operator who is a person without a fever (ACT 5601). This image forming operation includes a print operation, a scanning operation, a copy operation, an end operation, and the like. The print operation is an operation of designating a print operation which is an image formation based on the image data stored in the RAM 222 as an operation of the image forming apparatus 1, an operation of selecting image data to be image-formed from the image data stored in the RAM 222, an operation of designating the number of sheets to be printed, an operation of instructing the start of the print operation, and the like. The scanning operation includes an operation of designating a document reading operation using the image reading unit 11, an operation of designating a user terminal 2 for transmitting the scanned document image data, an operation of instructing the start of the scanning operation, and the like. The copy operation includes an operation of designating a copy operation of reading a document and forming an image based on the read document image data, an operation of designating the number of copies, an operation of instructing the start of the copy operation, and the like. The end operation includes an operation of instructing the end of the use of the image forming apparatus 1.

Hereinafter, only the operations related to image formation according to the print operation or the copy operation will be described.

The processor 21 determines whether or not the received operation is an end operation (ACT 5602). If it is an end operation (ACT 5602, YES), the processor 21 ends the subroutine of the image forming processing for a person without a fever and shifts to the process of ACT 1. Even if there is no operation by the liquid crystal touch panel 23 for a predetermined period such as 3 minutes, the processor 21 may end the subroutine of image forming processing for a person without a fever and shift to the process of ACT 1.

If it is determined that the received operation is not an end operation, that is, if it is determined that the operation instructing the start of the operation in the print operation or the copy operation was performed (ACT 5602, NO), the processor 21 starts the image forming operation by the image forming unit 18 (ACT 5603).

During this image forming operation, the processor 21 determines whether or not there is a remaining amount of toner contained in the toner cartridge 5 based on the output of the ATC sensor 40 (ACT 5604).

If it is determined that the toner cartridge 5 has a remaining amount of toner (ACT 5604, YES), the processor 21 determines whether or not there is a remaining amount of the print medium P which is the paper contained in the paper cassette 15 (ACT 5605).

If it is determined that there is paper in the paper cassette 15 (ACT 5605, YES), the processor 21 determines whether or not a paper jam of the conveyed paper, that is, the print medium P occurred somewhere in the conveyance unit 17 including the paper feed conveyance path 24 and the paper discharge conveyance path 25 (ACT 5606).

If it is determined that no paper jam occurred (ACT 5606, NO), the processor 21 determines whether or not the image formation was completed (ACT 5607). If it is determined that the image formation was not completed yet (ACT 5607, NO), the processor 21 shifts to the process of ACT 5604.

If it is determined that the toner cartridge 5 has no remaining amount of toner (ACT 5604, NO), the processor 21 stops the image forming operation (ACT 5608). Then, the processor 21 presents a replacement message requesting the replacement of the toner cartridge 5 to the operator (ACT 5609). For example, the processor 21 displays a replacement message such as "The toner has run out. Please replace it with a new toner cartridge" on the liquid crystal touch panel 23 of the operation unit 14, or causes the speaker 57 to output such a replacement message in audio. In response to the presentation of this replacement message, the operator opens the cover for the toner replacement provided on, for example, the front surface of the housing 10 and replaces the toner cartridge 5. Then, the operator touches the "start" key display on the liquid crystal touch panel 23 to instruct the restart of the image forming operation.

The processor 21 again determines whether or not there is a remaining amount of toner contained in the toner cartridge 5 based on the output of the ATC sensor 40 (ACT 5610). The processor 21 can determine whether or not the toner cartridge 5 was replaced, for example, by the output of a cartridge sensor (not shown) provided exclusively. If it is determined that there is no remaining amount of toner in the toner cartridge 5 (ACT 5610, NO), the processor 21 shifts to the process of ACT 5609. If it is determined that there is a remaining amount of toner in the toner cartridge 5 (ACT 5610, YES), the processor 21 resumes the image forming operation (ACT 5611). Then, the processor 21 shifts to the process of ACT 5605.

If it is determined that there is no paper in the paper cassette 15 (ACT 5604, YES), the processor 21 stops the image forming operation (ACT 5612). Then, the processor 21 presents a replenishment message requesting the replenishment of the print medium P to the paper cassette 15 to the operator (ACT 5613). For example, the processor 21 displays a replenishment message such as "There is no paper in the paper cassette. Please replenish the paper." on the liquid crystal touch panel 23 of the operation unit 14, or causes the speaker 57 to output such a replenishment message in audio. In response to the presentation of this replenishment message, the operator pulls out the paper cassette 15 from the housing 10, replenishes the print medium P, and then returns the paper cassette 15. Then, the operator touches the "start" key display on the liquid crystal touch panel 23 to instruct the restart of the image forming operation.

The processor 21 again determines whether or not there is a remaining amount of the print medium P contained in the paper cassette 15 (ACT 5614). If it is determined that there is no remaining amount of paper (ACT 5614, NO), the processor 21 shifts to the process of ACT 5613. If it is determined that there is paper in the paper cassette 15 (ACT 5614, YES), the processor 21 resumes the image forming operation (ACT 5615). Then, the processor 21 shifts to the process of ACT 5606.

Further, if it is determined that a paper jam occurred (ACT 5606, YES), the processor 21 stops the image forming operation (ACT 5616). Then, the processor 21 presents, to the operator, a paper removal message requesting the removal of the jammed print medium P from the conveyance unit 17 (ACT 5617). For example, the processor 21 displays a paper removal message such as "A paper jam has occurred. Please remove the jammed paper." on the liquid crystal touch panel 23 of the operation unit 14, or causes the speaker 57 to output such a removal message in audio. At this time, the liquid crystal touch panel 23 may schematically indicate where the paper jam occurred in the conveyance unit 17. In response to this paper removal message, the operator opens the front door and the side door of the housing 10 for accessing the conveyance unit 17 in the housing 10 and removes the jammed print medium P from the conveyance unit 17. Then, the operator touches the "start" key display on the liquid crystal touch panel 23 to instruct the restart of the image forming operation.

The processor 21 determines whether or not the paper jam was cleared (ACT 5618). If it is determined that the print medium P is still jammed in the conveyance unit 17 and the paper jam was not cleared (ACT 5618, YES), the processor 21 shifts to the process of ACT 5617. If it is determined that the paper jam was cleared (ACT 5618, YES), the processor 21 resumes the image forming operation (ACT 5619). Then, the processor 21 shifts to the process of ACT 5607.

Then, if it is determined that the image formation is completed (ACT 5607, YES), the processor 21 presents the operator with an end inquiry asking whether to end the operation (ACT 5620). For example, the processor 21 displays an end inquiry such as "Do you want to end the operation?" on the liquid crystal touch panel 23 of the operation unit 14, or causes the speaker 57 to output such an end inquiry in audio. After that, the processor 21 shifts to the process of ACT 5601.

Figure 16:
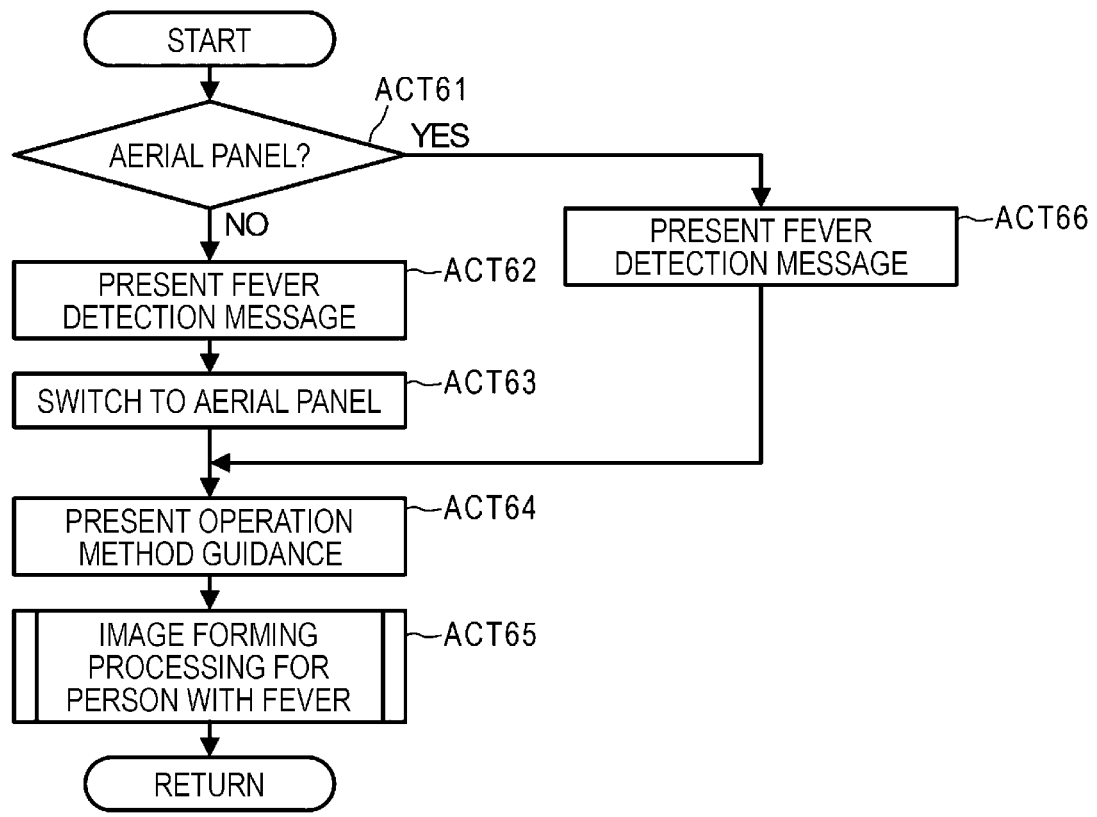
FIG. 16 is a flowchart showing an example of a subroutine of processing for a person with a fever in FIG. 12.

FIG. 16 is a flowchart showing an example of the subroutine of processing for a person with a fever of ACT 6. The processor 21 determines whether or not the operation unit 14 is in the aerial touch panel state in which the aerial touch panel projection image 55 is on the front side (ACT 61). If another operator who used the image forming apparatus 1 immediately before the operator, that is, the previous operator is a person with a fever, the operation unit 14 is in the aerial touch panel state.

If it is determined that the operation unit is not in the aerial touch panel state (ACT 61, NO), the processor 21 presents, to the operator, a person-with-fever detection message indicating that the operator is a person with a fever (ACT 62). For example, the processor 21 displays a person-with-fever detection message such as "The body temperature is detected to be high. The operation method will be changed to prevent infection." on the liquid crystal touch panel 23 of the operation unit 14, or causes the speaker 57 to output such a person-with-fever detection message in audio. After that, the processor 21 controls the operation unit rotating motor 50 by the operation unit rotating motor driver 66 to rotate and switch the operation unit 14 to the aerial touch panel state (ACT 63). Then, the processor 21 presents operation guidance indicating the operation method of the aerial touch panel to the operator (ACT 64). For example, the processor 21 displays the operation method guidance of the aerial touch panel projection image 55 by displaying "The operation has been switched to the aerial touch panel. You can operate by placing your finger on the button display unit" on the aerial liquid crystal display 53, or causes the speaker 57 to output such an operation method guidance in audio. Then, the processor 21 actually forms an image on the print medium P by a subroutine of image forming processing for a person with a fever as described later (ACT 65). After that, the processor 21 ends the subroutine of processing for a person with a fever and shifts to the process of ACT 1.

If it is determined that the operation unit is already in the aerial touch panel state (ACT 61, YES), the processor 21 presents the operation guidance indicating the operation method of the aerial touch panel to the operator (ACT 66). Then, the processor 21 shifts to the process of ACT 64.

Figure 17:
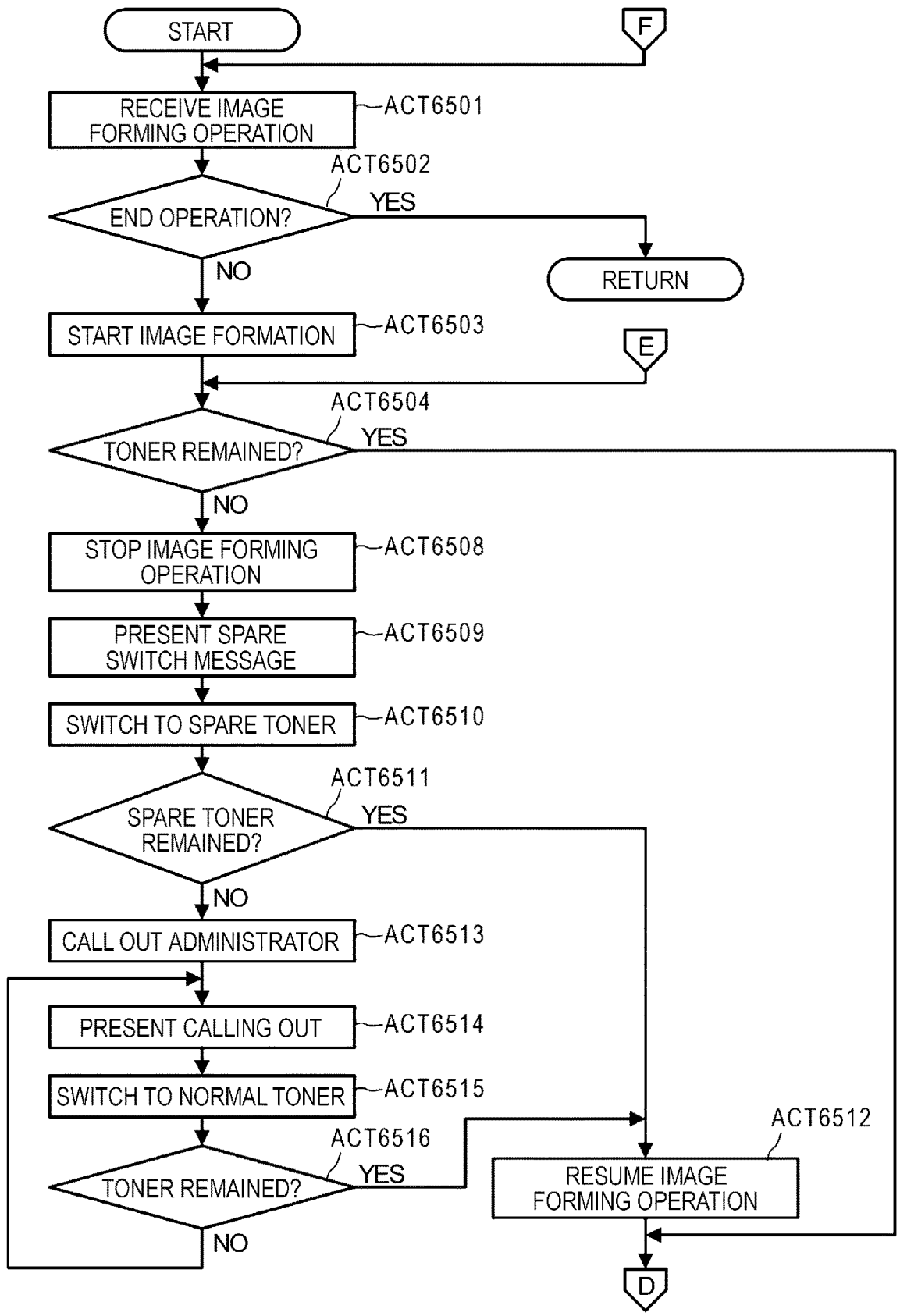
FIG. 17 is a flowchart showing an example of a subroutine of image forming processing for a person with a fever in FIG. 16.
Figure 18:
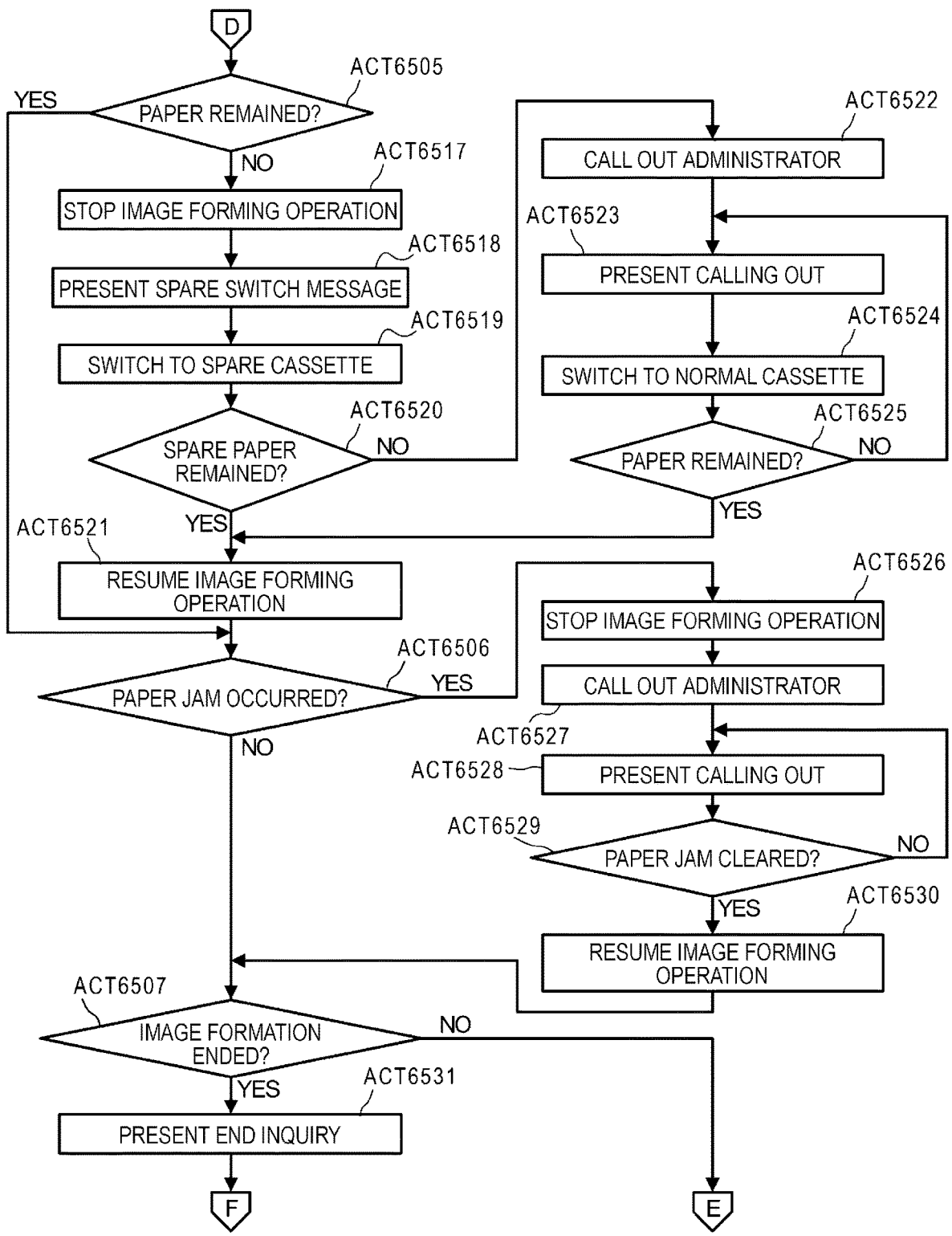
FIG. 18 is a flowchart showing an example of a subroutine of image forming processing for a person with a fever in FIG. 16.

FIGS. 17 and 18 are flowcharts showing an example of the subroutine of image forming processing for a person with a fever of ACT 65. First, the processor 21 accepts an image forming operation from the aerial touch panel by the operator who is a person with a fever (ACT 6501). This image forming operation is as described above in the description of the subroutine of image forming processing for a person without a fever. In this ACT 6501, the processor 21 determines the operation content of the operator based on the display content of the aerial liquid crystal display 53 and the aerial touch position by the aerial touch detection sensor 59. Hereinafter, only the operations related to image formation according to the print operation or the copy operation will be described.

The processor 21 determines whether or not the received operation is an end operation (ACT 6502). In the case of the end operation (ACT 6502, YES), the processor 21 ends the subroutine of the image forming processing for a person with a fever and shifts to the process of ACT 1. Even if there is no operation on the aerial touch panel for a predetermined period such as 3 minutes, the processor 21 may end the subroutine of image forming processing for a person with a fever and shift to the process of ACT 1.

If it is determined that the received operation is not an end operation, that is, if it is determined that the operation instructing the start of the operation in the print operation or the copy operation was performed (ACT 6502, NO), the processor 21 starts the image forming operation by the image forming unit 18 (ACT 6503).

During this image forming operation, the processor 21 determines whether or not there is a remaining amount of toner contained in the toner cartridge 5 based on the output of the ATC sensor 40 (ACT 6504).

If it is determined that the toner cartridge 5 has a remaining amount of toner (ACT 6504, YES), the processor 21 determines whether or not there is a remaining amount of the print medium P which is the paper contained in the paper cassette 15 (ACT 6505).

If it is determined that there is paper in the paper cassette 15 (ACT 6505, YES), the processor 21 determines whether or not a paper jam of the conveyed paper, that is, a print medium P occurred somewhere in the conveyance unit 17 including the paper feed conveyance path 24 and the paper discharge conveyance path 25 (ACT 6506).

If it is determined that no paper jam occurred (ACT 6506, NO), the processor 21 determines whether or not the image formation was completed (ACT 6507). If it is determined that the image formation was not completed yet (ACT 6507, NO), the processor 21 shifts to the process of ACT 6504.

If it is determined that there is no remaining amount of toner in the toner cartridge 5 (ACT 6504, NO), the processor 21 stops the image forming operation (ACT 6508). Then, the processor 21 presents, to the operator, a spare switching message for notifying the switch to the spare toner cartridge 5R (ACT 6509). For example, the processor 21 displays a spare switching message on the aerial touch panel projection image 55 by displaying such as "The toner has run out. Please wait as the toner will be switched to spare toner. ★★ Please do not touch the machine ★★" on the aerial liquid crystal display 53, or causes the speaker 57 to output such a spare switching message in audio.

Then, the processor 21 switches the toner cartridge to the spare toner cartridge 5R (ACT 6510). That is, the processor 21 controls the spare toner cartridge rotating motor 36R by the spare toner cartridge rotating motor driver 65 to supply the toner of the spare toner cartridge 5R to the developer container 37.

Here, the processor 21 determines whether or not there is a remaining amount of toner contained in the spare toner cartridge 5R based on the output of the ATC sensor 40 (ACT 6511). If it is determined that there is a remaining amount of toner in the spare toner cartridge 5R (ACT 6511, YES), the processor 21 resumes the image forming operation (ACT 6512). Then, the processor 21 shifts to the process of ACT 6505.

On the other hand, if it is determined that there is no remaining amount of toner in the switched spare toner cartridge 5R (ACT 6511, NO), the processor 21 performs a call-out of the administrator to the administrator terminal 4 by the communication interface 12 according to the contact information of the administrator stored in the NVM 223 (ACT 6513). This administrator call includes a message requesting the replacement of the toner cartridge 5 and the spare toner cartridge 5R.

Then, the processor 21 presents a calling message to the operator to notify that the administrator is being called out because there is no spare toner (ACT 6524). For example, the processor 21 displays a calling message on the aerial touch panel projection image 55 by displaying such as "The spare toner has run out. Please wait for a while as the administrator will replace it. ★★ Please do not touch the machine ★★" on the aerial liquid crystal display 53, or causes the speaker 57 to output such a calling message in audio. In response to this administrator call, the administrator opens the cover for the toner replacement provided, for example, on the front surface of the housing 10, and replaces the toner cartridge 5 and the spare toner cartridge 5R. Then, the administrator or the operator touches the "start" key display on the aerial touch panel in the air to instruct the restart of the image forming operation.

If the toner cartridge 5 and the spare toner cartridge 5R are replaced in this way, the processor 21 switches the toner cartridge to the replaced normal toner cartridge 5 (ACT 6515). That is, the processor 21 controls the toner cartridge rotating motor 36 by the toner cartridge rotating motor driver 64 to supply the toner of the toner cartridge 5 to the developer container 37. After that, the processor 21 determines whether or not there is a remaining amount of toner contained in the toner cartridge 5 based on the output of the ATC sensor 40 (ACT 6516). If it is determined that there is a remaining amount of toner in the toner cartridge 5 (ACT 6516, YES), the processor 21 shifts to the process of ACT 6512. If it is determined that there is no remaining amount of toner in the toner cartridge 5 (ACT 6516, NO), the processor 21 shifts to the process of ACT 6514.

Basically, the administrator replaces both the toner cartridge 5 and the spare toner cartridge 5R. In many cases, the toner cartridge 5 whose replacement frequency is higher than that of the spare toner cartridge 5R is stocked in advance for replacement. On the other hand, the spare toner cartridge 5R, which is less frequently replaced, may be out of stock. In such a case, only the toner cartridge 5 is replaced, and the spare toner cartridge 5R is replaced at a later date. Therefore, in the above-mentioned processing for a person without a fever of ACT 5, the operator is presented with an opportunity to replace the spare toner cartridge 5R so that the spare toner cartridge 5R can be replaced if the spare toner cartridge 5R is in stock.

If it is determined that there is no paper in the paper cassette 15 (ACT 6505, NO), the processor 21 stops the image forming operation (ACT 6517). Then, the processor 21 presents, to the operator, a spare switching message for notifying the switch to the spare paper cassette 15R (ACT 6518). For example, the processor 21 displays a spare switching message on the aerial touch panel projection image 55 by displaying such as "The paper has run out. Please wait as it is to switch to a spare cassette. ★★ Please do not touch the machine ★★" on the aerial liquid crystal display 53, or causes the speaker 57 to output such a spare switching message in audio.

Then, the processor 21 switches to the spare paper cassette 15R (ACT 6519). That is, the processor 21 controls the spare paper cassette paper feed motor 68 by the spare paper cassette paper feed motor driver 62 to supply the print medium P contained in the spare paper cassette 15R to the conveyance unit 17.

Here, the processor 21 determines whether or not the spare paper cassette 15R has a remaining amount of the spare paper, that is, the print medium P, based on the output of the spare paper cassette remaining amount detection sensor 63 (ACT 6520). If it is determined that the spare paper cassette 15R has a remaining amount of spare paper (ACT 6520, YES), the processor 21 resumes the image forming operation (ACT 6521). Then, the processor 21 shifts to the process of ACT 6506.

On the other hand, if it is determined that there is no spare paper remaining in the switched spare paper cassette 15R (ACT 6520, NO), the processor 21 performs a call-out of the administration to the administrator terminal 4 by the communication interface 12 according to the contact information of the administrator stored in the NVM 223 (ACT 6522). This administrator call includes a message requesting replenishment of the print medium P to the paper cassette 15 and the spare paper cassette 15R.

Then, the processor 21 presents a calling message to the operator to notify that the administrator is being called because there is no spare paper (ACT 6523). For example, the processor 21 displays a calling message on the areal touch panel projection image 55 by displaying such as "The paper in the spare cassette has run out. Please wait for a while as the administrator will replenish it. ★★ Please do not touch the machine ★★" on the aerial liquid crystal display 53, or causes the speaker 57 to output such a calling message in audio. In response to this call, the administrator holds the opening and closing operation unit of the paper cassette 15 provided on the front surface of the housing 10, pulls out the paper cassette 15, replenishes the print medium P, and then returns the paper cassette 15. Further, the administrator holds the opening and closing operation unit of the spare paper cassette 15R, pulls out the spare paper cassette 15R from the housing 10, replenishes the print medium P, and then returns the spare paper cassette 15R. Then, the administrator or the operator touches the "start" key display on the aerial touch panel in the air to instruct the restart of the image forming operation.

If the print medium P is replenished to the paper cassette 15 and the spare paper cassette 15R by the administrator in this way, the processor 21 switches to the normal paper cassette 15 to which the print medium P is replenished (ACT 6524). That is, the processor 21 controls the paper cassette paper feed motor 67 by the paper cassette paper feed motor driver 60 to supply the print medium P contained in the paper cassette 15 to the conveyance unit 17. After that, the processor 21 determines whether or not the paper cassette 15 has a remaining amount of paper based on the output of the paper cassette remaining amount detection sensor 61 (ACT 6525). If it is determined that the paper cassette 15 has a remaining amount of paper (ACT 6525, YES), the processor 21 shifts to the process of ACT 6521. If it is determined that there is no remaining amount of paper in the paper cassette 15 (ACT 6525, NO), the processor 21 shifts to the process of ACT 6523.

Basically, the administrator supplies the print medium P to both the paper cassette 15 and the spare paper cassette 15R. However, there may be a case where the print medium P is replenished only to the paper cassette 15 and the spare paper cassette 15R is not replenished with paper. Therefore, in the above-mentioned processing for a person without a fever of ACT 5, the operator is presented with an opportunity to replenish the spare paper cassette 15R so that the spare paper cassette 15R can be replenished with the print medium P.

Further, if it is determined that a paper jam occurred (ACT 6506, YES), the processor 21 stops the image forming operation (ACT 6526). Then, the processor 21 performs a call-out of the administrator to the administrator terminal 4 by the communication interface 12 according to the contact information of the administrator stored in the NVM 223 (ACT 6527). This administrator call includes a message requesting to clear the paper jam.

Then, the processor 21 presents a calling message to the operator to notify that the administrator is being called due to a paper jam (ACT 6528). For example, the processor 21 displays a calling message on the aerial touch panel projection image 55 by displaying such as "A paper jam has occurred. Please wait for a while as the administrator will remove it. ★★ Please do not touch the machine ★★" on the aerial liquid crystal display 53, or causes the speaker 57 to output such a calling message in audio. In response to this call, the administrator opens the conveyance unit access cover provided, for example, on the front surface or the side surface of the housing 10 to remove the jammed print medium P from the conveyance unit 17. Then, the administrator or the operator touches the "start" key display on the liquid crystal touch panel 23 to instruct the restart of the image forming operation.

The processor 21 determines whether or not the paper jam was cleared (ACT 6529). If it is determined that the print medium P is still jammed in the conveyance unit 17 and the paper jam was not cleared (ACT 6529, NO), the processor 21 shifts to the process of ACT 6528. If it is determined that the paper jam was cleared (ACT 6529, YES), the processor 21 resumes the image forming operation (ACT 6530). Then, the processor 21 shifts to the process of ACT 6507.

Then, if it is determined that the image formation was completed (ACT 6507, YES), the processor 21 presents the operator with an end inquiry asking whether to end the operation (ACT 6531). For example, the processor 21 displays an end inquiry on the aerial touch panel projection image 55 by displaying such as "Do you want to end the operation?" on the aerial liquid crystal display 53, or causes the speaker 57 to output such an end inquiry in audio. After that, the processor 21 shifts to the process of ACT 6501.

As described above, the image forming apparatus 1 according to the embodiment includes the infrared thermography camera 20 as a body surface temperature measuring sensor that measures the body surface temperature of the operator in a non-contact manner, the operation unit 14 as a user interface that presents a message to the operator, the communication interface 12 for transmitting a message to the administrator who manages the image forming apparatus 1, and the processor 21 as a controller. Then, when access to the surface or the inside of the housing 10 of the image forming apparatus 1 is required and the body surface temperature of the operator is equal to or higher than a threshold temperature, the processor 21 transmits, via the communication interface 12, a message requesting the administrator to contact the surface or the inside of the image forming apparatus 1, for example, to the administrator terminal 4 operated by the administrator, and presents, on the operation unit 14, a message requesting not to touch the image forming apparatus 1 to the operator.

According to such a configuration, if a state in which access to the surface or the inside of the housing 10 of the image forming apparatus 1 is required occurs and the operator has a fever, since a message is presented to the operator so as not to touch the image forming apparatus 1, it is possible to prevent virus adhesion to the surface or the inside of the housing 10 of the image forming apparatus 1 due to the touch to the surface or the inside of the housing 10 of the image forming apparatus 1 during the replenishment or replacement work of consumables. Therefore, it is possible to prevent the secondary virus adhesion to a person without an infectious disease who uses the image forming apparatus 1 after an operator who has a high fever due to an infectious disease.

The message presented to the operator by the processor 21 can include a message requesting not to contact the image forming apparatus 1 since the administrator was already requested to contact the surface or the inside of the housing 10 of the image forming apparatus 1.

In this way, it is possible to prevent the operator from walking around in search of the administrator by presenting a message that the administrator was already requested, in addition to requesting the administrator to contact the surface or the inside of the housing 10 of the image forming apparatus 1, for example, to the administrator terminal 4 operated by the administrator. Therefore, it is possible to prevent an operator who has a high fever due to an infectious disease from walking around and spreading the virus.

Further, the state in which access to the surface or the inside of the housing 10 of the image forming apparatus 1 is required includes a state in which consumables need to be replaced or replenished, and if the body surface temperature of the operator is equal to or higher than a threshold temperature, the processor 21 transmits a message requesting the administrator to replace or replenish the consumables via the communication interface 12.

Therefore, if it is necessary to replace or replenish consumables such as toner and the print medium P, it is possible to prevent the operator who has a high fever due to an infectious disease from contacting the cover for the toner replacement for taking out the toner cartridge 5 housed in the housing 10 of the image forming apparatus 1 and the opening and closing operation unit of the paper cassette 15 exposed on the surface of the housing 10 of the image forming apparatus 1.

The image forming apparatus 1 according to the embodiment further includes the toner cartridge 5 and the paper cassette 15 which are normal containers for storing consumables, and the spare toner cartridge 5R and the spare paper cassette 15R which are spare containers for storing spare consumables. Then, if the remaining amount of consumables held in the toner cartridge 5 or the paper cassette 15 reaches the remaining amount requiring replacement or replenishment, the processor 21 switches the container to be used from the toner cartridge 5 or the paper cassette 15 to the spare toner cartridge 5R or the spare paper cassette 15R if the body surface temperature of the operator is equal to or higher than a threshold temperature.

According to such a configuration, if the toner of the toner cartridge 5 or the print medium P of the paper cassette 15 runs out and the operator is a person with a fever, since the toner cartridge or the paper cassette is switched to the spare toner cartridge 5R or the spare paper cassette 15R, it is possible to prevent a person with a fever from touching the surface or the inside of the housing 10 of the image forming apparatus 1 for the replacement or replenishment work of consumables. Therefore, it is possible to prevent the secondary infection to a person without an infectious disease who uses the image forming apparatus 1 thereafter.

The processor 21 determines that the consumables need to be replaced or replenished if the remaining amount of the consumables held in the spare container switched from the normal container reaches the remaining amount requiring replacement or replenishment, and transmits, to the administrator, a message requesting to replace or replenish the consumables by the communication interface 12.

Therefore, even if the operator has a fever, it is possible to wait until the consumables held in the spare container run out without transmitting the message to the administrator if the consumables held in the normal container ran out. Thus, the work frequency of the administrator can be reduced.

Here, if the body surface temperature of the operator is lower than the threshold temperature, the processor 21 presents, to the operator, a message urging to replace the spare container or replenish the spare container with consumables by the operation unit 14 if the remaining amount of consumables held in the spare container reaches the remaining amount requiring replacement or replenishment.

Therefore, the work frequency of the administrator can be reduced by requesting the operator who has no fever to replace the spare container or replenish the consumables with the spare container.

Further, if the normal container was switched to the spare container, if the body surface temperature of the operator is lower than the threshold temperature, the processor 21 switches the spare container to the normal container and the operation unit 14 presents, to the operator, a message urging to replace the switched container or replenish the container with consumables.

Therefore, after the image formation operation using the spare container for a person with a fever is completed, the operator who has no fever is requested to replace the spare container or replenish the consumables to the spare container. Thus, the work frequency of the administrator can be reduced.

Further, a state in which access to the surface or the inside of the housing 10 of the image forming apparatus 1 is required includes a state in which a paper jam occurs in the middle of the conveyance unit 17 including the paper feed conveyance path 24 and the paper discharge conveyance path 25, which are conveyance paths of the print medium P, which is paper on which an image is formed, and if the body surface temperature of the operator is equal to or higher than the threshold temperature, the processor 21 transmits a message requesting the administrator to remove the jammed paper by the communication interface 12.

Therefore, if a paper jam occurs, it is possible to prevent the operator who has a high fever due to an infectious disease from contacting the conveyance unit access cover provided, for example, on the front surface or the side surface of the housing 10 for accessing the conveyance unit 17.

Further, in the image forming apparatus 1 according to the embodiment, the operation unit 14 includes the liquid crystal touch panel 23 that displays a message to the operator and detects a touch position by the operator, and the aerial touch panel which is composed of, for example, the aerial liquid crystal display 53, the aerial touch panel 3D plate 54, the aerial touch detection sensor 59, and the like, projects a message to an operator in the air and detects an aerial touch position by the operator. Then, if the body surface temperature of the operator is equal to or higher than the threshold temperature, the processor 21 switches the operation unit 14 from the liquid crystal touch panel 23 to the aerial touch panel.

Therefore, an operator who has a high fever due to an infectious disease can input the operation without touching the normal liquid crystal touch panel 23 and it is possible to prevent the next operator from a secondary infection.

If the operation unit 14 is the aerial touch panel which was switched from the liquid crystal touch panel 23, the processor 21 switches the operation unit 14 from the aerial touch panel to the liquid crystal touch panel 23 if the body surface temperature of the operator is lower than the threshold temperature.

In this way, if the next operator has no fever, it is possible to return to the original liquid crystal touch panel 23.

In the above-described embodiment, the ATC sensor 40 is used to detect the remaining amount of toner in the toner cartridge 5 and the spare toner cartridge 5R, but each of the toner cartridges 5 and 5R may have a dedicated toner remaining amount sensor to allow the processor 21 to detect the remaining amount of toner by communicating with those toner remaining amount sensors.

Further, the function described in the above-described embodiment is not limited to the configuration using hardware and can be implemented by loading a program describing each function into a computer using software. Further, each function may be configured by appropriately selecting either software or hardware.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image forming apparatus, comprising:
    a body surface temperature measuring sensor that measures a body surface temperature of an operator in a non-contact manner;
    a user interface that presents a message to the operator;
    a communication interface that communicates with an administrator terminal communicable with the image forming apparatus; and
    a controller that transmits a message requesting to touch a surface or an inside of the image forming apparatus to the administrator by the communication interface and presents a message requesting not to touch the image forming apparatus to the operator by the user interface when access to the inside of the image forming apparatus is required and the body surface temperature of the operator is equal to or higher than a threshold temperature.

2. The image forming apparatus according to claim 1, wherein
    the message presented by the controller to the operator includes a message requesting not to access the image forming apparatus because the administrator previously requested to access the surface or the inside of the image forming apparatus.

3. The image forming apparatus according to claim 1, wherein
    the state in which access to the surface or the inside of the image forming apparatus is required includes a state in which consumables need to be replaced or replenished, and
    if the body surface temperature of the operator is equal to or higher than the threshold temperature, the controller transmits a message requesting replacement or replenishment of the consumables to the administrator by the communication interface.

4. The image forming apparatus according to claim 3, further comprising:
    a normal container for accommodating the consumables; and
    a spare container for accommodating the spare consumables, wherein
    if the remaining amount of the consumables held in the normal container reaches a remaining amount requiring replacement or replenishment and the body surface temperature of the operator is equal to or higher than the threshold temperature, the controller switches the container to be used from the normal container to the spare container.

5. The image forming apparatus according to claim 4, wherein
    if the remaining amount of the consumables held in the spare container switched from the normal container reaches the remaining amount requiring replacement or replenishment, the controller determines that the consumables need to be replaced or replenished and transmits the message requesting replacement or replenishment of the consumables to the administrator by the communication interface.

6. The image forming apparatus according to claim 4, wherein
    if the body surface temperature of the operator is lower than the threshold temperature, the controller presents, to the operator, a message urging replacement of the spare container or replenishment of the spare container with the consumables by the user interface if the remaining amount of the consumables held in the spare container reaches the remaining amount that needs to be replaced or replenished.

7. The image forming apparatus according to claim 4, wherein
    if the normal container previously switched to the spare container and the body surface temperature of the operator is lower than the threshold temperature,
    the controller switches the spare container to the normal container and presents, to the operator, a message urging replacement of the switched container or replenishment of the container with the consumables by the user interface.

8. The image forming apparatus according to claim 1, wherein
the state in which access to the surface or the inside of the image forming apparatus is required includes a state in which a paper jam occurs in the middle of the conveyance path of a paper on which an image is formed, and
the controller transmits, to the administrator, a message requesting to remove the jammed paper by the communication interface if the body surface temperature of the operator is equal to or higher than the threshold value.

9. The image forming apparatus according to claim 1, wherein
the user interface includes
a touch panel that displays a message to the operator and detects a touch position by the operator, and
an aerial touch panel that projects a message to the operator in air and detects the touch position in the air by the operator, and
the controller switches the user interface from the touch panel to the aerial touch panel if the body surface temperature of the operator is equal to or higher than the threshold temperature.

10. The image forming apparatus according to claim 9, wherein
if the user interface previously switched from the touch panel to the aerial touch panel, the controller switches the user interface from the aerial touch panel to the touch panel if the body surface temperature of the operator is lower than the threshold temperature.

11. A method for an image forming apparatus, comprising:
a body surface temperature measuring sensor that measuring a body surface temperature of an operator in a non-contact manner;
presenting a message to the operator via a user interface;
communicating with an administrator terminal communicable with the image forming apparatus by a communication interface; and
transmitting a message requesting to touch a surface or an inside of the image forming apparatus to the administrator by the communication interface and presenting a message requesting not to touch the image forming apparatus to the operator by the user interface when access to the inside of the image forming apparatus is required and the body surface temperature of the operator is equal to or higher than a threshold temperature.

12. The method according to claim 11, further comprising:
presenting to the operator a message requesting not to access the image forming apparatus because the administrator previously requested to access the surface or the inside of the image forming apparatus.

13. The method according to claim 11, wherein
the state in which access to the surface or the inside of the image forming apparatus is required includes a state in which consumables need to be replaced or replenished, and
further comprising:
if the body surface temperature of the operator is equal to or higher than the threshold temperature, transmitting a message requesting replacement or replenishment of the consumables to the administrator by the communication interface.

14. The method according to claim 13, wherein the image forming apparatus comprises a normal container for accommodating the consumables and a spare container for accommodating the spare consumables,
further comprising:
if the remaining amount of the consumables held in the normal container reaches a remaining amount requiring replacement or replenishment and the body surface temperature of the operator is equal to or higher than the threshold temperature, switching the container to be used from the normal container to the spare container.

15. The method according to claim 14, further comprising:
if the remaining amount of the consumables held in the spare container switched from the normal container reaches the remaining amount requiring replacement or replenishment, determining that the consumables need to be replaced or replenished and transmitting the message requesting replacement or replenishment of the consumables to the administrator by the communication interface.

16. The method according to claim 14, further comprising:
if the body surface temperature of the operator is lower than the threshold temperature, presenting, to the operator, a message urging replacement of the spare container or replenishment of the spare container with the consumables by the user interface if the remaining amount of the consumables held in the spare container reaches the remaining amount that needs to be replaced or replenished.

17. The method according to claim 14, further comprising:
if the normal container previously switched to the spare container and the body surface temperature of the operator is lower than the threshold temperature,
switching the spare container to the normal container and presenting, to the operator, a message urging replacement of the switched container or replenishment of the container with the consumables by the user interface.

18. The method according to claim 11, wherein
the state in which access to the surface or the inside of the image forming apparatus is required includes a state in which a paper jam occurs in the middle of the conveyance path of a paper on which an image is formed,
further comprising:
transmitting, to the administrator, a message requesting to remove the jammed paper by the communication interface if the body surface temperature of the operator is equal to or higher than the threshold value.

19. The method according to claim 11, wherein
the user interface includes
a touch panel that displays a message to the operator and detects a touch position by the operator, and
an aerial touch panel that projects a message to the operator in air and detects the touch position in the air by the operator,
further comprising:
switching the user interface from the touch panel to the aerial touch panel if the body surface temperature of the operator is equal to or higher than the threshold temperature.

20. The method according to claim 19, further comprising:
if the user interface previously switched from the touch panel to the aerial touch panel, switching the user interface from the aerial touch panel to the touch panel if the body surface temperature of the operator is lower than the threshold temperature.

* * * * *